United States Patent [19]

Hamprecht et al.

[11] Patent Number: 5,280,009
[45] Date of Patent: Jan. 18, 1994

[54] SUBSTITUTED PYRIMIDINE DERIVATIVES AND THEIR USE FOR CONTROLLING UNDESIRABLE PLANT GROWTH

[75] Inventors: Gerhard Hamprecht, Weinheim; Klaus Ditrich, Bad Duerkheim; Karl-Otto Westphalen, Speyer; Matthias Gerber, Mutterstadt; Helmut Walter, Obrigheim, all of Fed. Rep. of Germany

[73] Assignee: BASF Aktiengesellschaft, Ludwigshafen, Fed. Rep. of Germany

[21] Appl. No.: 913,654

[22] Filed: Jul. 16, 1992

[30] Foreign Application Priority Data

Jul. 16, 1991 [DE] Fed. Rep. of Germany ....... 4123525

[51] Int. Cl.$^5$ .......................................... C07D 413/12
[52] U.S. Cl. ................... 504/239; 544/320;
544/321; 544/324; 544/323; 544/235; 544/237;
544/354; 544/356; 544/284; 544/183; 544/90;
544/105; 544/63; 544/276; 544/277; 544/295;
544/296; 544/238; 544/212; 544/182; 544/96;
544/98; 544/122; 544/123; 504/242; 504/237;
504/235; 504/240; 504/228; 504/223; 504/225;
504/241; 504/230; 504/229
[58] Field of Search ............... 504/239, 242, 237, 228,
504/241; 544/320, 321, 323, 324, 122, 96, 238,
277, 105, 284, 237

[56] References Cited

U.S. PATENT DOCUMENTS

| | | | |
|---|---|---|---|
| 3,667,007 | 5/1972 | Kressel et al. | 317/235 |
| 3,892,554 | 7/1975 | Schneider | 260/256.4 N |
| 4,025,515 | 5/1977 | Schneider | 71/92 |
| 4,082,535 | 4/1978 | Hoegerle et al. | 71/92 |
| 4,523,945 | 6/1985 | Mengel et al. | 71/92 |
| 4,877,443 | 10/1989 | Schwamborn et al. | 71/92 |
| 4,941,910 | 7/1990 | Muller et al. | 71/92 |

FOREIGN PATENT DOCUMENTS

| | | |
|---|---|---|
| 2048713 | 2/1992 | Canada . |
| 254183 | 7/1987 | European Pat. Off. . |
| 3717480 | 12/1988 | Fed. Rep. of Germany . |
| 63-313777 | 12/1988 | Japan . |
| 1-250363 | 10/1989 | Japan . |
| 3-227978 | 10/1991 | Japan . |

OTHER PUBLICATIONS

Patent Abst. of Japan, vol. 13, No. 595, C672, Dec. 1989.

Chem. Abst., vol. 111, No. 28, Abst. No. 7430j, p. 715, 1989.

Chem. Abst., vol. 116, Abst. No. 83694s, p. 83693, 1992.

Primary Examiner—John M. Ford
Attorney, Agent, or Firm—Keil & Weinkauf

[57] ABSTRACT

Pyrimidine derivatives of the Formula Ia or Ib

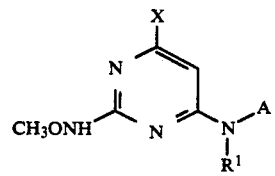

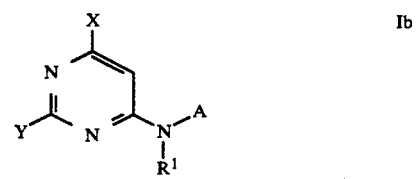

where the substituents have the following meanings:
$R^1$ is hydrogen or alkyl;
A is a substituted or unsubstituted bi- or tricyclic carbo- or heterocyclic radical which may contain one or several double bonds;
$R^5$ is H or alkyl;
X is halogen, alkyl, haloalkyl, alkoxy, haloalkoxy, alkylthio or haloalkylthio; and addition salts thereof with organic or inorganic acids and the use of said pyrimidine derivative to control undesirable plant growth.

10 Claims, No Drawings

SUBSTITUTED PYRIMIDINE DERIVATIVES AND THEIR USE FOR CONTROLLING UNDESIRABLE PLANT GROWTH

The present invention relates to novel pyrimidine derivatives of the formula I

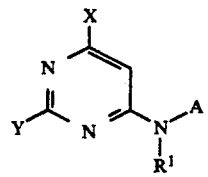

where $R^1$ is hydrogen or $C_1$–$C_6$-alkyl;

A is a bi- or tricyclic carbo- or heterocyclic radical which may contain one or more double bonds and is unsubstituted or substituted by the following groups: $C_1$–$C_3$-alkyl, $C_1$–$C_3$-alkoxy or halogen, or is $CR^2R^3R^4$, in which $R^2$ and $R^3$ are each hydrogen or $C_1$–$C_4$-alkyl which is unsubstituted or carries from one to three of the following groups: $C_1$–$C_4$-alkoxy, $C_1$–$C_4$-alkylthio or halogen and $R^4$ is unsubstituted or substituted naphthyl with the exception of 1-naphthyl; unsubstituted or substituted $C_4$–$C_8$-cycloalkyl, or cyclopropyl if Y is $NH_2$ and X is not trifluoromethyl; unsubstituted or substituted bicycloalkyl or mono- or bicyclic heterocyclyl having from 1 to 3 hetero atoms selected from the group consisting of oxygen, sulfur and nitrogen, with the exception of 2-furyl, 2-thienyl, 2-pyrrolyl, 2-N-methylpyrrolyl, 2,3-pyridyl, 2-thiolanyl, 2-perhydropyrrolyl and 2-perhydro-N-methylpyrrolyl and, if $R^2$ and $R^3$ are each hydrogen and Y is not an $NH(C_1$–$C_4$-alkoxy) and furthermore if Y is an $NH(C_1$–$C_4$-alkoxy), $R_4$ is substituted or unsubstituted bicycloalkyl or mono- or bicyclic heterocyclyl having from 1 to 3 heteroatoms selected from the group consisting of oxygen, sulfur and nitrogen;

phenyl if $R^2$ or $R^3$ is substituted by halogen, methoxy or methylthio or if Y is $NH_2$ and at the same time X is $C_1$–$C_3$-haloalkyl or $C_1$–$C_3$-haloalkoxy or if Y is mono- or di-$C_1$–$C_6$-alkylamino and at the same time X is $C_1$–$C_3$-haloalkoxy, where the phenyl radical may carry the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro or cyano; $C_2$–$C_6$-alkyl, $C_2$–$C_6$-alkenyl or $C_2$–$C_6$-alkinyl if Y is $NH(C_1$–$C_4$-alkoxy) and at the same time X is chlorine or $C_1$–$C_3$-haloalkyl;

X is halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio or $C_1$–$C_3$-haloalkylthio;

Y is halogen, $C_1$–$C_3$-alkyl, $C_1$–$C_3$-haloalkyl, $C_1$–$C_3$-alkylthio or, if A is a thienylethyl or furylethyl radical or a bicyclic radical, with the exception of naphthyl, quinolyl and isoquinolyl, or $R^2$ is trifluoromethyl, $R^3$ is hydrogen and $R^4$ is a phenyl radical substituted as stated above, Y may furthermore be $C_1$–$C_4$-alkoxy, $C_1$–$C_3$-alkoxy-$C_2$-or -$C_3$-alkoxy or $C_1$–$C_3$-alkylthio-$C_2$- or -$C_3$-alkoxy, or Y is $NR^5R^6$, in which $R^5$ is hydrogen, $C_1$–$C_6$-alkyl, $C_1$–$C_3$-haloalkyl, $C_1$–$C_4$-alkoxy, $C_1$–$C_3$-alkoxy-$C_1$–$C_3$-alkyl or $C_3$–$C_6$-cycloalkyl and $R^6$ is hydrogen, except when $R^5$ is methoxy and $R^4$ is phenyl, or $C_1$–$C_4$-alkyl, and addition salts thereof with organic or inorganic acids.

The present invention furthermore relates to a process for the preparation of the pyrimidine derivatives and the use thereof controlling undesirable plant growth.

A number of pyrimidine derivatives having herbicidal activity are known. DE-A 20 65 629 and DE-A 20 06 145 describe herbicidal 2-amino-6-chloropyrimidine derivatives having an alkyl, allyl or cyclohexylamino group in the 4-position.

Further herbicidal derivatives are disclosed in DE-A 26 30 140, DE-A 36 01 800, EP-A 254 183, EP-A 332 963, Japanese Preliminary Published Applications J 01-250-363 (27.12.88) and J 63-313-777 (17.06.87) and DE-A 37 17 480. However, these compounds are inadequate owing to the unsatisfactory selectivity with respect to weeds.

It is an object of the present invention to provide novel compounds from the class consisting of substituted pyrimidines having improved herbicidal properties.

We have found that this object is achieved by the pyrimidines defined at the outset.

We have also found compounds of the formula I and salts thereof have good selectivity with respect to weeds in crops such as cereals and corn.

Salts are understood as meaning addition salts of the following inorganic and organic acids:

Hydrohalic acids, such as hydrochloric and hydrobromic acid, phosphoric acid, sulfuric acid, fluoboric acid ($HBF_4$), perchloric acid, alkylsulfuric acids, such as methyl- or ethylsulfuric acid, naphthoic acids, benzoic acid, halobenzoic acids, acetic acid, haloacetic acids, such as trichloroacetic acid, aminoacetic acid, propionic acid, halopropionic acids, butyric acid, lactic acid, stearic acid, aliphatic dicarboxylic acids, such as oxalic acid, tartaric acid or maleic acid, aromatic sulfonic acids, such as p-toluenesulfonic acid, etc.

With the optically active compounds of the formula I the invention embraces both the racemates and the possible enantiomers.

Pyrimidine derivatives which are preferred herbicidal active ingredients are those of the formula I in which $R^1$ is hydrogen.

Other preferred pyrimidine derivatives of the formula I are those in which $R^1$ is hydrogen, X is halogen, Y is $NHR^5$, where $R^5$ is hydrogen, $C_1$–$C_6$-alkyl, $C_1$–$C_3$-alkoxy-$C_1$–$C_3$-alkyl or $C_1$–$C_4$-alkoxy, except for methoxy when $R^4$ is phenyl, A is a bi- or tricyclic, carbo- or heterocyclic radical which may contain one or more double bonds and is unsubstituted or substituted by methyl, methoxy or halogen, or A is $CHR^3R^4$, where $R^3$ is hydrogen, $C_1$–$C_4$-alkyl or trifluoromethyl and $R^4$ has the abovementioned meanings.

Particular preference is given to pyrimidine derivatives of the formula I where $R^1$ is hydrogen;

X is chlorine;

Y is $NH_2$;

a is a $CHR^3R^4$ group;

$R^3$ is hydrogen or $C_1$–$C_4$-alkyl;

$R^4$ is 2-naphthyl, $C_3$–$C_8$-cycloalkyl, bicyclo[2.2.1]hept-2-yl, 2-benzofuryl, 3-thienyl, 2-tetrahydrofuryl, 2-indanyl, 2-tetrahydroindanyl or 3-benzopyranyl; or $R^1$ is hydrogen;
X is chlorine;
Y is $NH(C_1-C_4)$-alkoxy;
A is a $CHR^3R^4$ group;
$R^3$ is hydrogen or $C_1-C_4$-alkyl;
$R^4$ is 1-naphthyl, $C_3-C_8$-cycloalkyl, phenyl, 3-chlorophenyl, 2-furyl, 3-(1-methylethyl)iosoxazol-5-yl, 3-thienyl, 3-tetrahydrofuryl or 2-tetrahydroindanyl; or $R^1$ is hydrogen;
X is trifluoromethoxy;
Y is $NH_2$;
A is a $CHR^3R^4$ group;
$R^3$ is hydrogen or $C_1-C_4$-alkyl;
$R^4$ is 1-naphthyl, $C_3-C_8$-cylcoalkyl, phenyl, 3-thienyl or 2-benzofuranyl; or $R^1$ is hydrogen;
X is trifluoromethyl;
Y is $NH_2$;
A is a $CHR^3R^4$ group;
$R^3$ is hydrogen or $C_1-C_4$-alkyl;
$R^4$ is 1-naphthyl, $C_3-C_8$-cycloalkyl, phenyl, 3-thienyl, 2-tetrahydrofuryl or 1-indanyl.

The present invention furthermore relates to a process for the preparation of these compounds and herbicides which contain one or more compounds I in which the substituents have the abovementioned meanings.

The novel pyrimidine derivatives can be prepared by various methods; they are obtainable, for example, by the following processes:

1. By reacting a pyrimidine of the formula II

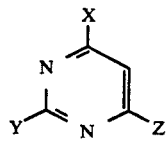

II where X and Y have the abovementioned meanings and Z is a nucleophilically substitutable group, such as halogen, such as fluorine, chlorine or bromine, with an amine of the formula III

III where $R^1$ and A have the abovementioned meanings.

The reaction is advantageously carried out by a method in which a pyrimidine of the formula II in an inert organic solvent is initially taken, a mixture of amine III with an organic base is added and the reaction is then completed at elevated temperatures.

The mixture can be worked up in a conventional manner, for example by extraction with water to remove the hydrochloride of the base, filtering off the product under suction or extracting it with an organic solvent and evaporating the organic solvent.

Solvents such as halohydrocarbons, e.g. tetrachloroethane, methylene chloride, chloroform, dichloroethane, chlorobenzene and 1,2-dichlorobenzane, ethers, e.g. diethyl ether, methyl tert-butyl ether, dimethoxyethane, diethylene glycol diethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidionone and 1,3-dimethylimidazolin-2-one, aromatics, e.g. benzene, toluene, xylene, pyridine and quinoline, ketones, e.g. acetone and methyl ethyl ketone, alcohols, e.g. ethanol, propanol and isopropanol, and corresponding mixtures are advantageously used for these reactions.

The reaction can be carried out at from 50° C. to the reflux temperature of the particular solvent or solvent mixture, preferably at from 70° to 150° C.

The molar ratios in which the required starting compounds are reacted with one another are from 0.9:1 to 1.3:1 for the ratio of amine III or organic base to pyrimidine II. However, the amine III can also be used in an excess of about 2 mol per mol of pyrimidine.

The concentration of the educts in the solvent (mixture) is in general from 0.1 to 5, preferably from 0.2 to 2, mol/l.

2. A further process for the preparation of the compounds of the formula I is based on the reaction of a pyrimidine of the formula IV, where X has the abovementioned meanings and Z is halogen, initially with a first nucleophile of the formula V, where Y is an abovementioned oxygen- or nitrogen-bound radical, to give a compound of the formula II, which is then reacted with an amine of the formula III to give the end products I.

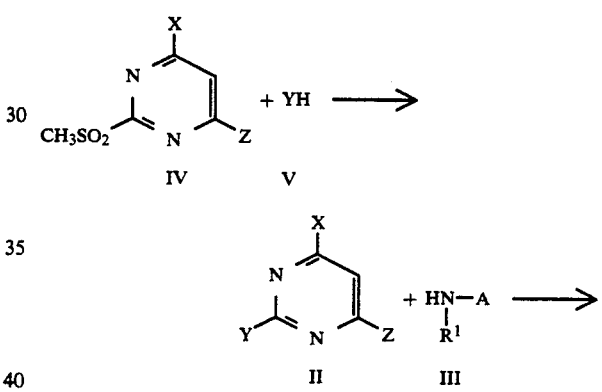

Solvents such as halohydrocarbons, e.g. tetrachloroethane, methylene chloride, chloroform, chlorobenzene and 1,2-dichlorobenzene, ethers, e.g. diethyl ether, methyl tert-butyl ether, dimethoxyethane, diethylene glycol dimethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, e.g. benzene, toluene, xylene, pyridine and quinoline, ketones, e.g. acetone, methyl ethyl ketone, alcohols, e.g. ethanol, propanol and isopropanol and corresponding mixtures are advantageously used for these reactions.

It is occasionally useful to carry out the first reaction step in the presence of an acid acceptor.

Preferably used acid acceptors are aromatic nitrogen bases, such as pyridine, 4-dimethylaminopyridine and quinoline, tertiary aliphatic amines, such as triethylamine, N-ethyldiisopropylamine and N-methylmorpholine, bi- and tricyclic amines, such as diazabicyclooctane (DABCO) and diazabicycloundecane (DBU), and also carbonates and bicarbonates of alkali or alkaline earth metals, e.g. sodium carbonate, potassium carbonate, sodium bicarbonate and potassium bicarbonate. It is sometimes also useful to use combination of the abovementioned bases.

The molar ratio in which nucleophile V and acid acceptor are used is in general from 1:0.5 to 1:5.

The reaction can be carried out at from −80° to 150° C., preferably from −80° to 60° C., in the first stage and then follows process I in the second stage.

The molar ratios in which the required starting compounds are reacted with one another are in general from 0.9:1 to 1.2:1 for the ratio of nucleophile V to pyrimidine IV.

The concentration of the educts in the solvent (mixture) is in general from 0.1 to 5, preferably from 0.2 to 2, mol/l.

After the end of the reaction, the reaction mixture of the first stage is washed with water, dried and evaporated down.

3. A further process for the preparation of compounds of the formula Ia

[Structure Ia]

$R^4$ = heterocyclic structure where X, Y, $R^1$, $R^2$ and $R^3$ have the above meanings and $R^4$ is a five-membered heterocyclic radical comprises reacting an alkyne of the formula VI

[Structure VI]

which can be prepared by process 1 or 2 and in which X, Y, $R^1$, $R^2$ and $R^3$ have the abovementioned meanings and $R^5$ is hydrogen or $C_1$–$C_4$-alkyl, with a 1,3-dipole VII $$a \overset{\oplus}{=} b \overset{\ominus}{-} c \qquad \text{VII}$$

by a cycloaddition reaction. The 1,3-dipoles VII can be produced and reacted by known methods (cf. A. Padwa, 1,3-Dipolar Cycloaddition Chemistry, Wiley, New York 1984).

The process for the preparation of compounds of the formula Ib

[Structure Ib]

where X, Y, $R^1$, $R^2$, $R^3$ and $R^5$ have the abovementioned meanings and $R^6$ is hydrogen, halogen, $C_1$–$C_4$-alkyl or unsubstituted or substituted phenyl, may be mentioned here by way of example.

In the procedure adopted here, an alkyne of the formula VI, where the substituents have the above meanings, is reacted with a hydroxamyl chloride of the formula VIII, where $R^6$ has the above meanings, in the presence of a nitrogen base.

[Structure VI]

[Structure VIII] $\xrightarrow{\text{nitrogenbase}}$ Ib

In an advantageous procedure, the alkyne VI in an inert organic solvent is initially taken, about molar amounts of the hydroxamyl chloride VIII are added and about twice the molar amount of a base is then added dropwise. The mixture can be worked up in a conventional manner, for example by hydrolysis with water and filtering off the product under suction or extracting it with an organic solvent.

Advantageously used solvents for these reactions are halohydrocarbons, such as dichloroethane, chlorobenzene, 1,2-dichlorobenzene, tetrachloroethane, dichloromethane and chloroform, ethers, such as diethyl ether, methyl tert-butyl ether, dimethoxyethane, diethylene glycol dimethyl ether, tetrahydrofuran and dioxane, and aromatics, such as benzene, toluene and xylene, and mixtures of these solvents.

The reactions can be carried out at from −10° to 50° C., preferably from 0° to 30° C.

Preferred bases are nitrogen bases, such as 2-, 3- or 4-picoline, N,N-dimethylaniline, N,N-dimethylcyclohexylamine, triethylamine (TEA), pyridine and 1,8-diazabicyclo[5.4.0]undec-7-ene (DBU).

The reactants are used in particular in a molar ratio of 1:1, and the nitrogen base is added in an amount corresponding to from twice to three times the molar amount.

The concentration of the educts in the solvent mixture is in general from 0.1 to 5, preferably from 0.2 to 2, mol/l.

In view of the intended use of the compounds I, examples of suitable substituents are the following radicals:

$R^1$ is hydrogen, $C_1$–$C_6$-alkyl, such as methyl, ethyl, propyl, 2-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1,2,3-trimethylpropyl, 1-ethyl-1-methylpropyl or 1-ethyl-2-methylpropyl, in particular methyl, ethyl, propyl, 1-methylethyl or 1,1-dimethylethyl;

A is a bi- or tricyclic carbo- or heterocyclic radical which is saturated or contains one or more double bonds, for example one which is aromatic and is selected from the group consisting of 2-, 3-, 4-, 5-, 6- and 7-benzofuryl, 1-, 3-, 4-, 5-, 6- and 7-isobenzofuryl, 2-, 3-, 4-, 5-, 6- and 7-benzo[b]thienyl, 1-, 3-, 4-, 5-, 6- and 7-benzo[c]thienyl, 2-, 3-, 4-, 5-, 6-and 7-indolyl, 1-, 3-, 4-, 5-, 6- and 7-isoindolyl, 3-, 4-, 5-, 6- and 7-benzo[c]isoxazolyl, 3-, 4-, 5-, 6- or 7-benzo[b]isoxazolyl, 3-, 4-, 5-, 6- or 7-benzo[c]isothiazolyl, 3-, 4-, 5-, 6- or 7-benzo[b]isothiazolyl, 3-, 4-, 5-, 6- or 7-benzo[b]pyrazolyl, 3-, 4-, 5-, 6- or 7-benzo[c]pyrazolyl, 2-, 4-, 5-, 6- or 7-benzoxazolyl, 2-, 4-, 5-, 6- or 7-benzothiazolyl, 2-, 4-, 5- or 6-benzimidazolyl, 2,3-dihydrobenzofur-2-, 3-, 4-, 5-, 6- or 7-yl, 1,3-dihydroisobenzofur-1-, 3-, 4-, 5-, 6- or 7-yl, 2,3-dihydrobenzo[b]thien-2-, 3-, 4-, 5-, 6- or 7-yl, 1,3-dihydrobenzo[c]thien-1-, 3-, 4-, 5-, 6- or 7-yl, 1,3-dihydrobenzo[c]thien-1-, 3-, 4-, 5-, 6- or 7-yl, 1,3-dihydroisoindol-1-, 3-, 4-, 5-, 6- or 7-yl, 2,3-dihydroindol-2-, 3-, 4-, 5-, 6- or 7-yl, 2-, 3-, 4-, 5-, 6-, 7- or 8-chromenyl, 1-, 3-, 4-, 5-, 6-, 7- or 8-isochromenyl, 2-, 3-, 4-, 5-, 6-, 7- or 8-quinolyl, 1-, 3-, 4-, 5-, 6-, 7- or 8-isoquinolyl, 2-, 3-, 4-, 5-, 6-, 7- or 8-chromanyl, 1-, 3-, 4-, 5-, 6-, 7- or 8-isochromanyl, 3-, 4-, 5, 6-, 7- or 8-cinnolinyl, 1-, 4-, 5-, 6-, 7- or 8-phthalazinyl, 2-, 3-, 5-, 6-, 7- or 8-quinoxalinyl, 2-, 4-, 5-, 6-, 7- or 8-quinazolinyl, 3-, 5-, 6-, 7- or 8-benzo-1,2,4-triazinyl, 2-, 3-, 4-, 5-, 6- or 7-benzopyranyl, 2-, 3-, 4-, 5-, 6- or 7-naphthpyridinyl, 2-, 3-, 4-, 6-, 7- or 8-pyrido[3,2-b]pyridinyl, 2-, 3-, 4-, 5-, 7- or 8-pyrido[4,3-b]pyridinyl, 2-, 3-, 4-, 5-, 6- or 8-pyrido[3,4-b]pyridinyl, 1,3,2-benzoxazin-2-, 4-, 5-, 6-, 7- or 8-yl, 1,4,2-benzoxazin-2-, 3-, 5-, 6-, 7- or 8-yl, 2,3-1-benzoxazin-1-, 4-, 5-, 6-, 7- or 8-yl, 3,1,4-benzoxazin-2-, 4-, 5-, 6-, 7- or 8-yl, 1,2-benzisoxazin-3-, 4-, 5-, 6-, 7- or 8-yl, 1,4-benzisoxazin-2-, 3-, 5-, 6-, 7- or 8-yl, 2-, 6- or 8-purinyl, 1-, 2-, 3-, 4-, 5-, 6- or 7-indanyl, 1-, 2-, 3-, 4-, 5-, 6- or 7-indenyl, 1-, 2-, 3-, 4-, 5-, 6-, 7- or 8-tetralinyl, 1-, 2-, 3-, 4-, 5-, 6-, 7- or 8-decalinyl, 3-, 4-, 5-, 7-, 8-, 9-or 10-tricyclo-[5.2.1.0$^{2,6}$]decanyl, 3-, 4-, 5-, 7-, 8-, 9- or 10-tricyclo[5.2.1.0$^{2,6}$]dec-2,6-enyl, 1- or 2-norbornyl, 2-bornyl, 2- or 3-norpinyl, 1-, 2-, 3-, 4-, 5-, 6-, 7-, 8- or 9-fluorenyl or 1-, 2-, 3-, 4-, 5-, 6-, 7- or 8-naphthyl, where the stated radicals may carry from one to three of the following groups:

$C_1$–$C_3$-alkyl, such as methyl, ethyl, propyl or 1-methylethyl, $C_1$–$C_3$-alkoxy, such as methoxy, ethoxy, propoxy or 1-methylethoxy, or halogen, such as fluorine, chlorine, bromine or iodine, in particular fluorine or chlorine; $R^2$ and $R^3$ are each hydrogen, $C_1$–$C_4$-alkyl, such as methyl, ethyl, propyl, 1-methylethyl, butyl, 1-methylpropyl, 2-methylpropyl or 1,1-dimethylethyl, in particular methyl, ethyl, propyl or 1-methylethyl, which may carry from one to three of the following groups:

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy, propoxy or 1-methylethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio, ethylthio, propylthio or 1-methylethylthio;

halogen, such as fluorine, chlorine, bromine, iodine, in particular fluorine or chlorine;

$R^4$ is substituted 1-naphthyl or 2-naphthyl or, if Y is NH$_2$ and X is not trifluoromethyl, $R^4$ is cyclopropyl;

$C_4$–$C_8$-cycloalkyl, such as cyclobutyl, cyclopentyl, cyclohexyl, cycloheptyl or cyclooctyl, in particular cyclopentyl or cyclohexyl, mono- or bicyclic heterocyclyl having 1 to 3 hetero atoms selected from the group consisting of oxygen, sulfur and nitrogen, such as 2-furyl, 2-thienyl, 2-pyrrolyl, 2-N-methylpyrrolyl, 2- or 3-pyridyl, 2-thiolanyl, 2-perhydropyrrolyl or 2-perhydro-N-methylpyrrolyl, where $R^2$ and $R^3$ cannot simultaneously be hydrogen, or 2,3-tetrahydrofuryl, 3-furyl, 3-perhydropyrrolyl, 3-pyrrolyl, 3-thiolanyl, 3-thienyl, 2-, 3- or 4-pyranyl, 2-, 3- or 4-dihydropyranyl, 2-, 3- or 4-tetrahydropyranyl, 2-, 3- or 4-thiopyranyl, 2-, 3- or 4-tetrahydrothiopyranyl, 4-pyridyl, 3-, 4- or 5-isoxazolyl, 3-, 4-or 5-isothiazolyl, 2-, 4- or 5-oxazolyl, 2-, 4-or 5-thiazolyl, 2-, 4- or 5-imidazolyl, 3- or 4-pyrazolyl, 2-pyrazinyl, 2-, 4- or 5-pyrimidinyl, 2- or 3-pyridazinyl, 2- or 3-dioxolanyl, 1,2,3-thiadiazol-4- or 5-yl, 1,2,3-oxadiazol-4-or 5-yl, 1,2,4-oxadiazol-3- or 5-yl, 1,3,4-oxadiazol-2-or 5-yl, 1,3-dioxin-2-, 4-, 5- or 6-yl, 1,3-dioxan-2-, 4-, 5- or 6-yl, 1,4-dioxan-2-, 3-, 5-or 6-yl, 1,3,5-triazin-2-, 4- or 6-yl, 1,2,4-triazin-3-, 5- or 6-yl, 1,2,4-oxazin-3-, 4-, 5- or 6-yl, 1,3,2-oxazin-2-, 4-, 5- or 6-yl, 1,3,6-oxazin-2-, 4-, 5- or 6-yl, 1,2,6-oxazin-3-, 4-, 5- or 6-yl or 1,4-oxazin-2-, 3-, 5- or 6-yl, and the heterocycles and bialicycles which are stated for A and may carry from one to three of the following groups:

$C_1$–$C_3$-alkyl, such as methyl, ethyl, propyl or 1-methylethyl, $C_1$–$C_3$-alkoxy, such as methoxy, ethoxy, propoxy or 1-methylethoxy, halogen, such as fluorine, chlorine, bromine or iodine, in particular fluorine or chlorine, or phenyl which may carry the following groups: methyl, ethyl, trifluoromethyl, methoxy, ethoxy, difluoromethoxy, trifluoromethoxy, chlorodifluoromethoxy, methylthio, difluoromethylthio, trifluoromethylthio, chlorodifluoromethylthio, halogen, nitro or cyano;

X is halogen as stated above, in paritcular chlorine or bromine, $C_1$–$C_3$-alkyl as stated above, in particular methyl or ethyl, $C_1$–$C_3$-haloalkyl, such as trifluoromethyl, chlorodifluoromethyl, tetrafluoroethyl or pentafluoroethyl, in particular trifluoromethyl or chlorodifluoromethyl;

$C_1$–$C_3$-alkoxy as stated above, in particular methoxy or ethoxy;

$C_1$–$C_3$-haloalkyl, such as difluoromethoxy, trifluoromethoxy, chlorodifluoromethoxy, tetrafluoroethoxy or pentafluoroethoxy, in particular difluoromethoxy, trifluoromethoxy or chlorodifluoromethoxy; $C_1$–$C_3$-alkylthio, as stated above, in particular methylthio or ethylthio; $C_1$–$C_3$-haloalkylthio, such as difluoromethylthio, trifluoromethylthio, chlorodifluoromethylthio, tetrafluoroethylthio or pentafluoroethylthio, in particular difluoromethylthio, trifluoromethylthio or chlorodifluoromethylthio;

Y is halogen as stated above, in particular chlorine or bromine; $C_1$–$C_3$-alkyl as stated above, in particular methyl or ethyl; $C_1$–$C_4$-alkoxy as stated above, in particular methoxy, ethoxy or propoxy; $C_1$–$C_3$-alkoxy-$C_2$- or -$C_3$-alkoxy, such as methoxyethoxy, ethoxyethoxy, methoxypropoxy or ethoxyethoxy, in particular methoxyethoxy or ethoxyethoxy; $C_1$–$C_3$-alkylthio as stated above, in particular methylthio or ethylthio; $C_1$–$C_3$-haloalkyl as stated above, in particular trifluoromethyl; $C_1$–$C_3$-alkylthio-$C_2$- or $C_3$-alkoxy, such as methylthioethoxy, ethylthioethyxy or methylthiopropoxy, in particular methylthioethoxy or ethylthioethoxy;

$R^5$ is hydrogen, $C_1$–$C_6$-alkyl as stated for $R^1$, in particular methyl, ethyl, propyl or 1-methylethyl, $C_1$–$C_4$-alkoxy as stated above, in particular methoxy, ethoxy or propoxy, $C_1$–$C_3$-alkoxy-$C_2$- or $C_3$-alkyl, such as methoxyethyl, methoxypropyl, ethoxyethyl or ethoxypropyl, in particular methoxyethyl, or $C_3$–$C_8$-cycloalkyl as stated for $R^4$, in particular cyclopropyl, cyclopentyl or cyclohexyl;

$R^6$ is hydrogen or $C_1$–$C_4$-alkyl as stated above, in particular methyl or ethyl.

The pyrimidine derivatives I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are suitable for the preparation of solutions, emulsions, pastes and oil dispersions to be sprayed direct. Examples of suitable inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.02 to 95, and preferably 0.5 to 90, % by weight of active ingredient. The active ingredients are used in a purity of from 90 to 100, and preferably from 95 to 100, % (according to the NMR spectrum).

The compounds I according to the invention may be formulated for example as follows:

I. 90 parts by weight of compound no. 19 is mixed with 10 parts by weight of N-methyl-alpha-pyrrolidone. A mixture is obtained which is suitable for application in the form of very fine drops.

II. 20 parts by weight of compound no. 10 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 20 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 13 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 19 is well mixed with 3 parts by weight of the sodium salt of diisobutylnapthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 10 is intimately mixed with 97 parts by weight of particulate kaolin. A dust is obtained containing 3% by weight of the active ingredient.

VII. 30 parts by weight of compound no. 20 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 13 is intimately mixed with 2 parts of the calcium salt of dodecylbenzenesulfonic acid, 8 parts of a fatty alcohol polyglycol ether, 2 parts of the sodium salt of a phenol-sulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5, preferably 0.01 to 2, kg of active ingredient per hectare.

In view of the numerous application methods possible, the compounds according to the invention may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica rapa var. silvestris | |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossipium hirsutum (Gossypium arboreum Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To increase the spectrum of action and to achieve synergistic effects, the pyrimidine derivatives I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, trizines, amides, ureas, diphenyl ethers, triazinones, uracils, benzofuran derivatives, cyclohexane-1,3-dione derivatives, quinolinecarboxylic acids, sulfonylurea derivatives, (hetero)-aryloxyphenoxypropionic acids and salts, esters, amides thereof, etc.

It may also be useful to apply the pyrimidine derivatives of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Examples of herbicidally effective compounds having the general structure I are given below:

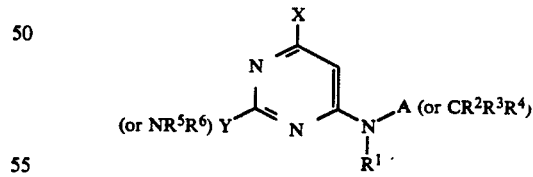

where
X is a radical from the group Q1 to Q30
Y is a radical from the group L1 to L32
$R^1$ is a radical from the group M1 to M34
A is a radical from the group N1 to N317
$R^2$ is a radical from the group O1 to O33
$R^3$ is a radical from the group P1 to P33
$R^4$ is a radical from the group R1 to R150
$R^5$ is a radical from the group S1 to S53
$R^6$ is a radical from the group T1 to T9
and the radicals Q, L, M, N, O, P, R, S and T may be combined at will and have the following meanings:

| Comp. No. | X |
|---|---|
| Q 1 | Cl |
| Q 2 | Br |
| Q 3 | I |
| Q 4 | F |
| Q 5 | $CH_3$ |
| Q 6 | $C_2H_5$ |
| Q 7 | $n\text{-}C_3H_7$ |
| Q 8 | $i\text{-}C_3H_7$ |
| Q 9 | $CF_3$ |
| Q 10 | $CF_2Cl$ |
| Q 11 | $HCF_2CF_2$ |
| Q 12 | $CF_2CF_3$ |
| Q 13 | $CH_3O$ |
| Q 14 | $C_2H_5O$ |
| Q 15 | $n\text{-}C_3H_7O$ |
| Q 16 | $i\text{-}C_3H_7O$ |
| Q 17 | $HCF_2O$ |
| Q 18 | $CF_3O$ |
| Q 19 | $CF_2ClO$ |
| Q 20 | $HCF_2CF_2O$ |
| Q 21 | $CF_3CF_2O$ |
| Q 22 | $CH_3S$ |
| Q 23 | $C_2H_5S$ |
| Q 24 | $n\text{-}C_3H_7S$ |
| Q 25 | $i\text{-}C_3H_7S$ |
| Q 26 | $HCF_2S$ |
| Q 27 | $CF_3S$ |
| Q 28 | $CF_2ClS$ |
| Q 29 | $HCF_2CF_2S$ |
| Q 30 | $CF_3CF_2S$ |
|  | Y |
| L 1 | Cl |
| L 2 | Br |
| L 3 | I |
| L 4 | F |
| L 5 | $CH_3$ |
| L 6 | $C_2H_5$ |
| L 7 | $n\text{-}C_3H_7$ |
| L 8 | $i\text{-}C_3H_7$ |
| L 9 | $CH_3O$ |
| L 10 | $C_2H_5O$ |
| L 11 | $n\text{-}C_3H_7O$ |
| L 12 | $i\text{-}C_3H_7O$ |
| L 13 | $n\text{-}C_4H_9O$ |
| L 14 | $sec\text{-}C_4H_9O$ |
| L 15 | $tert.\text{-}C_4H_9O$ |
| L 16 | $i\text{-}C_4H_9O$ |
| L 17 | $CH_3O[CH_2]_2O$ |
| L 18 | $CH_3O\text{—}[CH_2]_3O$ |
| L 19 | $C_2H_5O[CH_2]_2O$ |
| L 20 | $n\text{-}C_3H_7O[CH_2]_2O$ |
| L 21 | $i\text{-}C_3H_7O[CH_2]_2O$ |
| L 22 | $CH_3S$ |
| L 23 | $C_2H_5S$ |
| L 24 | $n\text{-}C_3H_7S$ |
| L 25 | $i\text{-}C_3H_7S$ |
| L 26 | $CF_3$ |
| L 27 | $CF_2Cl$ |
| L 28 | $HCF_2CF_2$ |
| L 29 | $CF_3CF_2$ |
| L 30 | $CF_3[CF_2]_2$ |
| L 31 | $CH_3S[CH_2]_2O$ |
| L 32 | $CH_3S[CH_2]_3O$ |
|  | $R^1$ |
| M 1 | H |
| M 2 | $CH_3$ |
| M 3 | $C_2H_5$ |
| M 4 | $n\text{-}C_3H_7$ |
| M 5 | $i\text{-}C_3H_7$ |
| M 6 | $n\text{-}C_4H_9$ |
| M 7 | $i\text{-}C_4H_9$ |
| M 8 | $sek.\text{-}C_4H_9$ |
| M 9 | $tert.\text{-}C_4H_9$ |
| M 10 | $n\text{-}C_5H_{11}$ |
| M 11 | $CH[CH_3]C_3H_7$ |
| M 12 | $CH_2CH[CH_3]C_2H_5$ |
| M 13 | $[CH_2]_2CH[CH_3]CH_3$ |
| M 14 | $C[CH_3]_2C_2H_5$ |
| M 15 | $CH[CH_3]CH[CH_3]CH_3$ |
| M 16 | $CH_2\text{—}C[CH_3]_2CH_3$ |
| M 17 | $CH[C_2H_5]C_2H_5$ |
| M 18 | $n\text{-}C_6H_{13}$ |
| M 19 | $CH[CH_3]C_4H_9$ |
| M 20 | $CH_2CH[CH_3]C_3H_7$ |
| M 21 | $[CH_2]_2CH[CH_3]C_2H_5$ |
| M 22 | $[CH_2]_3CH[CH_3]CH_3$ |
| M 23 | $C[CH_3]_2C_3H_7$ |
| M 24 | $CH[CH_3]CH[CH_3]C_2H_5$ |
| M 25 | $CH[CH_3]CH_2CH[CH_3]_2$ |
| M 26 | $CH_2\text{—}C[CH_3]_2C_2H_5$ |
| M 27 | $CH_2CH[CH_3]CH[CH_3]_2$ |
| M 28 | $[CH_2]_2C[CH_3]_2CH_3$ |
| M 29 | $CH[C_2H_5][CH_2]_2CH_3$ |
| M 30 | $CH_2CH[C_2H_5]C_2H_5$ |
| M 31 | $CH[CH_3]C[CH_3]_2CH_3$ |
| M 32 | $CH[CH_3]CH[CH_3]CH_2CH_3$ |
| M 33 | $C[CH_3, C_2H_5]C_2H_5$ |
| M 34 | $C[C_2H_5]CH[CH_3]_2$ |
|  | A |
| N 1 | 2-Benzofuryl |
| N 2 | 3-Benzofuryl |
| N 3 | 4-Benzofuryl |
| N 4 | 5-Benzofuryl |
| N 5 | 6-Benzofuryl |
| N 6 | 7-Benzofuryl |
| N 7 | 1-Isobenzofuryl |
| N 8 | 3-Isobenzofuryl |
| N 9 | 4-Isobenzofuryl |
| N 10 | 5-Isobenzofuryl |
| N 11 | 6-Isobenzofuryl |
| N 12 | 7-Isobenzofuryl |
| N 13 | 2-Benzo[b]thienyl |
| N 14 | 3-Benzo[b]thienyl |
| N 15 | 4-Benzo[b]thienyl |
| N 16 | 5-Benzo[b]thienyl |
| N 17 | 6-Benzo[b]thienyl |
| N 18 | 7-Benzo[b]thienyl |
| N 19 | 1-Benzo[c]thienyl |
| N 20 | 3-Benzo[c]thienyl |
| N 21 | 4-Benzo[c]thienyl |
| N 22 | 5-Benzo[c]thienyl |
| N 23 | 6-Benzo[c]thienyl |
| N 24 | 7-Benzo[c]thienyl |
| N 25 | 2-Indolyl |
| N 26 | 3-Indolyl |
| N 27 | 4-Indolyl |
| N 28 | 5-Indolyl |
| N 29 | 6-Indolyl |
| N 30 | 7-Indolyl |
| N 31 | 1-Isoindolyl |
| N 32 | 3-Isoindolyl |
| N 33 | 4-Isoindolyl |
| N 34 | 5-Isoindolyl |
| N 35 | 6-Isoindolyl |
| N 36 | 7-Isoindolyl |
| N 37 | 3-Benz[c]isoxazolyl |
| N 38 | 4-Benz[c]isoxazolyl |
| N 39 | 5-Benz[c]isoxazolyl |
| N 40 | 6-Benz[c]isoxazolyl |
| N 41 | 7-Benz[c]isoxazolyl |
| N 42 | 3-Benz[b]isoxazolyl |
| N 43 | 4-Benz[b]isoxazolyl |
| N 44 | 5-Benz[b]isoxazolyl |
| N 45 | 6-Benz[b]isoxazolyl |
| N 46 | 7-Benz[b]isoxazolyl |
| N 47 | 3-Benz[c]isothiazolyl |
| N 48 | 4-Benz[c]isothiazolyl |
| N 49 | 5-Benz[c]isothiazolyl |
| N 50 | 6-Benz[c]isothiazolyl |
| N 51 | 7-Benz[c]isothiazolyl |
| N 52 | 3-Benz[b]isothiazolyl |
| N 53 | 4-Benz[b]isothiazolyl |
| N 54 | 5-Benz[b]isothiazolyl |
| N 55 | 6-Benz[b]isothiazolyl |
| N 56 | 7-Benz[b]isothiazolyl |
| N 57 | 3-Benz[b]pyrazolyl |
| N 58 | 4-Benz[b]pyrazolyl |
| N 59 | 5-Benz[b]pyrazolyl |
| N 60 | 6-Benz[b]pyrazolyl |

-continued

| Comp. No. | |
|---|---|
| N 61 | 7-Benz[b]pyrazolyl |
| N 62 | 3-Benz[c]pyrazolyl |
| N 63 | 4-Benz[c]pyrazolyl |
| N 64 | 5-Benz[c]pyrazolyl |
| N 65 | 6-Benz[c]pyrazolyl |
| N 66 | 7-Benz[c]pyrazolyl |
| N 67 | 2-Benzoxazolyl |
| N 68 | 4-Benzoxazolyl |
| N 69 | 5-Benzoxazolyl |
| N 70 | 6-Benzoxazolyl |
| N 71 | 7-Benzoxazolyl |
| N 72 | 2-Benzthiazolyl |
| N 73 | 4-Benzthiazolyl |
| N 74 | 5-Benzthiazolyl |
| N 75 | 6-Benzthiazolyl |
| N 76 | 7-Benzthiazolyl |
| N 77 | 2-Benzimidazolyl |
| N 78 | 4-Benzimidazolyl |
| N 79 | 5-Benzimidazolyl |
| N 80 | 6-Benzimidazolyl |
| N 81 | 7-Benzimidazolyl |
| N 82 | 2-[2,3-Dihydro-benzofuryl] |
| N 83 | 3-[2,3-Dihydro-benzofuryl] |
| N 84 | 4-[2,3-Dihydro-benzofuryl] |
| N 85 | 5-[2,3-Dihydro-benzofuryl] |
| N 86 | 6-[2,3-Dihydro-benzofuryl] |
| N 87 | 7-[2,3-Dihydro-benzofuryl] |
| N 88 | 1-[1,3-Dihydro-isobenzofuryl] |
| N 89 | 3-[1,3-Dihydro-isobenzofuryl] |
| N 90 | 4-[1,3-Dihydro-isobenzofuryl] |
| N 91 | 5-[1,3-Dihydro-isobenzofuryl] |
| N 92 | 6-[1,3-Dihydro-isobenzofuryl] |
| N 93 | 7-[1,3-Dihydro-isobenzofuryl] |
| N 94 | 2-[2,3-Dihydro-benzo[b]thienyl] |
| N 95 | 3-[2,3-Dihydro-benzo[b]thienyl] |
| N 96 | 4-[2,3-Dihydro-benzo[b]thienyl] |
| N 97 | 5-[2,3-Dihydro-benzo[b]thienyl] |
| N 98 | 6-[2,3-Dihydro-benzo[b]thienyl] |
| N 99 | 7-[2,3-Dihydro-benzo[b]thienyl] |
| N 100 | 1-[1,3-Dihydro-benzo[c]thienyl] |
| N 101 | 3-[1,3-Dihydro-benzo[c]thienyl] |
| N 102 | 4-[1,3-Dihydro-benzo[c]thienyl] |
| N 103 | 5-[1,3-Dihydro-benzo[c]thienyl] |
| N 104 | 6-[1,3-Dihydro-benzo[c]thienyl] |
| N 105 | 7-[1,3-Dihydro-benzo[c]thienyl] |
| N 106 | 2-[2,3-Dihydro-indole] |
| N 107 | 3-[2,3-Dihydro-indole] |
| N 108 | 4-[2,3-Dihydro-indole] |
| N 109 | 5-[2,3-Dihydro-indole] |
| N 110 | 6-[2,3-Dihydro-indole] |
| N 111 | 7-[2,3-Dihydro-indole] |
| N 112 | 1-[1,3-Dihydro-isoindole] |
| N 113 | 3-[1,3-Dihydro-isoindole] |
| N 114 | 4-[1,3-Dihydro-isoindole] |
| N 115 | 5-[1,3-Dihydro-isoindole] |
| N 116 | 6-[1,3-Dihydro-isoindole] |
| N 117 | 7-[1,3-Dihydro-isoindole] |
| N 118 | 2-Chromenyl |
| N 119 | 3-Chromenyl |
| N 120 | 4-Chromenyl |
| N 121 | 5-Chromenyl |
| N 122 | 6-Chromenyl |
| N 123 | 7-Chromenyl |
| N 124 | 8-Chromenyl |
| N 125 | 1-Isochromenyl |
| N 126 | 3-Isochromenyl |
| N 127 | 4-Isochromenyl |
| N 128 | 5-Isochromenyl |
| N 129 | 6-Isochromenyl |
| N 130 | 7-Isochromenyl |
| N 131 | 8-Isochromenyl |
| N 132 | 2-Quinolyl |
| N 133 | 3-Quinolyl |
| N 134 | 4-Quinolyl |
| N 135 | 5-Quinolyl |
| N 136 | 6-Quinolyl |
| N 137 | 7-Quinolyl |
| N 138 | 8-Quinolyl |
| N 139 | 1-Isoquinolyl |
| N 140 | 3-Isoquinolyl |
| N 141 | 4-Isoquinolyl |
| N 142 | 5-Isoquinolyl |
| N 143 | 6-Isoquinolyl |
| N 144 | 7-Isoquinolyl |
| N 145 | 8-Isoquinolyl |
| N 146 | 2-Chromanyl |
| N 147 | 3-Chromanyl |
| N 148 | 4-Chromanyl |
| N 149 | 5-Chromanyl |
| N 150 | 6-Chromanyl |
| N 151 | 7-Chromanyl |
| N 152 | 8-Chromanyl |
| N 153 | 1-Isochromanyl |
| N 154 | 3-Isochromanyl |
| N 155 | 4-Isochromanyl |
| N 156 | 5-Isochromanyl |
| N 157 | 6-Isochromanyl |
| N 158 | 7-Isochromanyl |
| N 159 | 8-Isochromanyl |
| N 160 | 3-Cinnolinyl |
| N 161 | 4-Cinnolinyl |
| N 162 | 5-Cinnolinyl |
| N 163 | 6-Cinnolinyl |
| N 164 | 7-Cinnolinyl |
| N 165 | 8-Cinnolinyl |
| N 166 | 1-Phthalazinyl |
| N 167 | 4-Phthalazinyl |
| N 168 | 5-Phthalazinyl |
| N 169 | 6-Phthalazinyl |
| N 170 | 7-Phthalazinyl |
| N 171 | 8-Phthalazinyl |
| N 172 | 2-Quinoxalinyl |
| N 173 | 3-Quinoxalinyl |
| N 174 | 5-Quinoxalinyl |
| N 175 | 6-Quinoxalinyl |
| N 176 | 7-Quinoxalinyl |
| N 177 | 8-Quinoxalinyl |
| N 178 | 2-Quinazoline |
| N 179 | 4-Quinazoline |
| N 180 | 5-Quinazoline |
| N 181 | 6-Quinazoline |
| N 182 | 7-Quinazoline |
| N 183 | 8-Quinazoline |
| N 184 | 3-Benzo-1,2,4-triazinyl |
| N 185 | 5-Benzo-1,2,4-triazinyl |
| N 186 | 6-Benzo-1,2,4-triazinyl |
| N 187 | 7-Benzo-1,2,4-triazinyl |
| N 188 | 8-Benzo-1,2,4-triazinyl |
| N 189 | 2-Naphthyridinyl |
| N 190 | 3-Naphthyridinyl |
| N 191 | 4-Naphthyridinyl |
| N 192 | 5-Naphthyridinyl |
| N 193 | 6-Naphthyridinyl |
| N 194 | 7-Naphthyridinyl |
| N 195 | 2-Pyrido[3,4-b]pyridinyl |
| N 196 | 3-Pyrido[3,4-b]pyridinyl |
| N 197 | 4-Pyrido[3,4-b]pyridinyl |
| N 198 | 5-Pyrido[3,4-b]pyridinyl |
| N 199 | 6-Pyrido[3,4-b]pyridinyl |
| N 200 | 8-Pyrido[3,4-b]pyridinyl |
| N 201 | 2-Pyrido[3,2-b]pyridinyl |
| N 202 | 3-Pyrido[3,2-b]pyridinyl |
| N 203 | 4-Pyrido[3,2-b]pyridinyl |
| N 204 | 6-Pyrido[3,2-b]pyridinyl |
| N 205 | 7-Pyrido[3,2-b]pyridinyl |
| N 206 | 8-Pyrido[3,2-b]pyridinyl |
| N 207 | 2-Pyrido[4,3-b]pyridinyl |
| N 208 | 3-Pyrido[4,3-b]pyridinyl |
| N 209 | 4-Pyrido[4,3-b]pyridinyl |
| N 210 | 5-Pyrido[4,3-b]pyridinyl |
| N 211 | 7-Pyrido[4,3-b]pyridinyl |
| N 212 | 8-Pyrido[4,3-b]pyridinyl |
| N 213 | 2-[1,3,2-Benzoxazinyl] |
| N 214 | 4-[1,3,2-Benzoxazinyl] |
| N 215 | 5-[1,3,2-Benzoxazinyl] |
| N 216 | 6-[1,3,2-Benzoxazinyl] |
| N 217 | 7-[1,3,2-Benzoxazinyl] |
| N 218 | 8-[1,3,2-Benzoxazinyl] |
| N 219 | 2-[1,4,2-Benzoxazinyl] |
| N 220 | 3-[1,4,2-Benzoxazinyl] |
| N 221 | 5-[1,4,2-Benzoxazinyl] |
| N 222 | 6-[1,4,2-Benzoxazinyl] |

| Comp. No. | |
|---|---|
| N 223 | 7-[1,4,2-Benzoxazinyl] |
| N 224 | 8-[1,4,2-Benzoxazinyl] |
| N 225 | 1-[2,3,1-Benzoxazinyl] |
| N 226 | 4-[2,3,1-Benzoxazinyl] |
| N 227 | 5-[2,3,1-Benzoxazinyl] |
| N 228 | 6-[2,3,1-Benzoxazinyl] |
| N 229 | 7-[2,3,1-Benzoxazinyl] |
| N 230 | 8-[2,3,1-Benzoxazinyl] |
| N 231 | 2-[3,1,4-Benzoxazinyl] |
| N 232 | 4-[3,1,4-Benzoxazinyl] |
| N 233 | 5-[3,1,4-Benzoxazinyl] |
| N 234 | 6-[3,1,4-Benzoxazinyl] |
| N 235 | 7-[3,1,4-Benzoxazinyl] |
| N 236 | 8-[3,1,4-Benzoxazinyl] |
| N 237 | 3-[1,2-Benzisoxazinyl] |
| N 238 | 4-[1,2-Benzisoxazinyl] |
| N 239 | 5-[1,2-Benzisoxazinyl] |
| N 240 | 6-[1,2-Benzisoxazinyl] |
| N 241 | 7-[1,2-Benzisoxazinyl] |
| N 242 | 8-[1,2-Benzisoxazinyl] |
| N 243 | 2-[1,4-Benzisoxazinyl] |
| N 244 | 3-[1,4-Benzisoxazinyl] |
| N 245 | 5-[1,4-Benzisoxazinyl] |
| N 246 | 6-[1,4-Benzisoxazinyl] |
| N 247 | 7-[1,4-Benzisoxazinyl] |
| N 248 | 8-[1,4-Benzisoxazinyl] |
| N 249 | 2-Purinyl |
| N 250 | 6-Purinyl |
| N 251 | 8-Purinyl |
| N 252 | 1-Indanyl |
| N 253 | 2-Indanyl |
| N 254 | 3-Indanyl |
| N 255 | 4-Indanyl |
| N 256 | 5-Indanyl |
| N 257 | 6-Indanyl |
| N 258 | 7-Indanyl |
| N 259 | 1-Indenyl |
| N 260 | 2-Indenyl |
| N 261 | 3-Indenyl |
| N 262 | 4-Indenyl |
| N 263 | 5-Indenyl |
| N 264 | 6-Indenyl |
| N 265 | 7-Indenyl |
| N 266 | 1-Tetralinyl |
| N 267 | 2-Tetralinyl |
| N 268 | 3-Tetralinyl |
| N 269 | 4-Tetralinyl |
| N 270 | 5-Tetralinyl |
| N 271 | 6-Tetralinyl |
| N 272 | 7-Tetralinyl |
| N 273 | 8-Tetralinyl |
| N 274 | 1-Decalinyl |
| N 275 | 2-Decalinyl |
| N 276 | 3-Decalinyl |
| N 277 | 4-Decalinyl |
| N 278 | 5-Decalinyl |
| N 279 | 6-Decalinyl |
| N 280 | 7-Decalinyl |
| N 281 | 8-Decalinyl |
| N 282 | 3-Tricyclo[5.2.1.0$^{2,6}$]decanyl |
| N 283 | 4-Tricyclo[5.2.1.0$^{2,6}$]decanyl |
| N 284 | 5-Tricyclo[5.2.1.0$^{2,6}$]decanyl |
| N 285 | 7-Tricyclo[5.2.1.0$^{2,6}$]decanyl |
| N 286 | 8-Tricyclo[5.2.1.0$^{2,6}$]decanyl |
| N 287 | 9-Tricyclo[5.2.1.0$^{2,6}$]decanyl |
| N 288 | 10-Tricyclo[5.2.1.0$^{2,6}$]decanyl |
| N 289 | 3-Tricyclo[5.2.1.0$^{2,6}$]dec-2$^6$-enyl |
| N 290 | 4-Tricyclo[5.2.1.0$^{2,6}$]dec-2$^6$-enyl |
| N 291 | 5-Tricyclo[5.2.1.0$^{2,6}$]dec-2$^6$-enyl |
| N 292 | 7-Tricyclo[5.2.1.0$^{2,6}$]dec-2$^6$-enyl |
| N 293 | 8-Tricyclo[5.2.1.0$^{2,6}$]dec-2$^6$-enyl |
| N 294 | 9-Tricyclo[5.2.1.0$^{2,6}$]dec-2$^6$-enyl |
| N 295 | 10-Tricyclo[5.2.1.0$^{2,6}$]dec-2$^6$-enyl |
| N 296 | 1-Norbornyl |
| N 297 | 2-Norbornyl |
| N 298 | 2-Bornyl |
| N 299 | 2-Norpinyl |
| N 300 | 3-Norpinyl |
| N 301 | 1-Fluorenyl |
| N 302 | 2-Fluorenyl |
| N 303 | 3-Fluorenyl |
| N 304 | 4-Fluorenyl |
| N 305 | 5-Fluorenyl |
| N 306 | 6-Fluorenyl |
| N 307 | 7-Fluorenyl |
| N 308 | 8-Fluorenyl |
| N 309 | 9-Fluorenyl |
| N 310 | 1-Naphthyl |
| N 311 | 2-Naphthyl |
| N 312 | 3-Naphthyl |
| N 313 | 4-Naphthyl |
| N 314 | 5-Naphthyl |
| N 315 | 6-Naphthyl |
| N 316 | 7-Naphthyl |
| N 317 | 8-Naphthyl |
| | $R^2$ |
| O 1 | $CH_3$ |
| O 2 | $C_2H_5$ |
| O 3 | $n-C_3H_7$ |
| O 4 | $i-C_3H_7$ |
| O 5 | $n-C_4H_9$ |
| O 6 | $sec.-C_4H_9$ |
| O 7 | $tert.-C_4H_9$ |
| O 8 | $[CH_2]_2OCH_3$ |
| O 9 | $[CH_2]_2OC_2H_5$ |
| O 10 | $[CH_2]_2O-i-C_3H_7$ |
| O 11 | $[CH_2]O-n-C_3H_7$ |
| O 12 | $[CH_2]_2SCH_3$ |
| O 13 | $[CH_2]_2SC_2H_5$ |
| O 14 | $[CH_2]_2S-n-C_3H_7$ |
| O 15 | $[CH_2]_2S-i-C_3H_7$ |
| O 16 | $CHF_2$ |
| O 17 | $CF_2Cl$ |
| O 18 | $CF_3$ |
| O 19 | $CH_2CF_3$ |
| O 20 | $CF_2CF_2H$ |
| O 21 | $CF_2CF_3$ |
| O 22 | $[CF_2]_2CF_3$ |
| O 23 | $CH_2Cl$ |
| O 24 | $[CH_2]_2Cl$ |
| O 25 | $CH_2F$ |
| O 26 | $[CH_2]_2F$ |
| O 27 | $[CH_2]Br$ |
| O 28 | $CH_2—OCH_3$ |
| O 29 | $CH_2—O—C_2H_5$ |
| O 30 | $CH_2—O-n-C_3H_7$ |
| O 31 | $CH_2O-i-C_3H_7$ |
| O 32 | H |
| O 33 | $i-C_4H_9$ |
| | $R^3$ |
| P 1 | H |
| P 2 | $CH_3$ |
| P 3 | $C_2H_5$ |
| P 4 | $n-C_3H_7$ |
| P 5 | $i-C_3H_7$ |
| P 6 | $n-C_4H_9$ |
| P 7 | $i-C_4H_9$ |
| P 8 | $sec.-C_4H_9$ |
| P 9 | $tert.-C_4H_9$ |
| P 10 | $CH_2OCH_3$ |
| P 11 | $CH_2OC_2H_5$ |
| P 12 | $CH_2O-n-C_3H_7$ |
| P 13 | $CH_2O-i-C_3H_7$ |
| P 14 | $[CH_2]_2OCH_3$ |
| P 15 | $[CH_2]_2OC_2H_5$ |
| P 16 | $[CH_2]_2O-n-C_3H_7$ |
| P 17 | $[CH_2]_2O-i-C_3H_7$ |
| P 18 | $[CH_2]_2SCH_3$ |
| P 19 | $[CH_2]_2SC_2H_5$ |
| P 20 | $[CH_2]_2S-n-C_3H_7$ |
| P 21 | $[CH_2]_2S-i-C_3H_7$ |
| P 22 | $CHF_2$ |
| P 23 | $CF_2Cl$ |
| P 24 | $CF_3$ |
| P 25 | $CH_2CF_3$ |
| P 26 | $CF_2CF_2H$ |
| P 27 | $CF_2CF_3$ |
| P 28 | $[CH_2]_2CF_3$ |
| P 29 | $CH_2Cl$ |
| P 30 | $[CH_2]_2Cl$ |
| P 31 | $CH_2F$ |

-continued

| Comp. No. | |
|---|---|
| P 32 | [CH$_2$]$_2$F |
| P 33 | [CH$_2$]$_2$Br |
| | R$^4$ |
| R 1 | 1-Naphthyl |
| R 2 | 2-Naphthyl |
| R 3 | cycl.-C$_3$H$_5$ |
| R 4 | cycl.-C$_4$H$_7$ |
| R 5 | cycl.-C$_5$H$_9$ |
| R 6 | cycl.-C$_6$H$_{11}$ |
| R 7 | cycl.-C$_7$H$_{13}$ |
| R 8 | cycl.-C$_8$H$_{15}$ |
| R 9 | 2-Furyl |
| R 10 | 2-Thienyl |
| R 11 | 2-Pyrrolyl |
| R 12 | 2-N-Methylpyrrolyl |
| R 13 | 2-Pyridyl |
| R 14 | 3-Pyridyl |
| R 15 | 2-Thiolanyl |
| R 16 | 2-perhydro-pyrrolyl |
| R 17 | 2-Perhydro-N-methylpyrrolyl |
| R 18 | 2-Tetrahydrofuryl |
| R 19 | 3-Tetrahydrofuryl |
| R 20 | 3-Furyl |
| R 21 | 3-Perhydro-pyrrolyl |
| R 22 | 3-Pyrrolyl |
| R 23 | 3-Thiolanyl |
| R 24 | 3-Thienyl |
| R 25 | 2-Pyranyl |
| R 26 | 3-Pyranyl |
| R 27 | 4-Pyranyl |
| R 28 | 2-Tetrahydropyranyl |
| R 29 | 3-Tetrahydropyranyl |
| R 30 | 4-Tetrahydropyranyl |
| R 31 | 2-Thiopyranyl |
| R 32 | 3-Thiopyranyl |
| R 33 | 4-Thiopyranyl |
| R 34 | 2-Tetrahydro-thiopyranyl |
| R 35 | 3-Tetrahydro-thiopyranyl |
| R 36 | 4-Tetrahydro-thiopyranyl |
| R 37 | 4-Pyridyl |
| R 38 | 3-Isoxazolyl |
| R 39 | 4-Isoxazolyl |
| R 40 | 5-Isoxazolyl |
| R 41 | 3-Isothiazolyl |
| R 42 | 4-Isothiazolyl |
| R 43 | 5-Isothiazolyl |
| R 44 | 2-Oxazolyl |
| R 45 | 4-Oxazolyl |
| R 46 | 5-Oxazolyl |
| R 47 | 2-Thiazolyl |
| R 48 | 4-Thiazolyl |
| R 49 | 5-Thiazolyl |
| R 50 | 2-Imidazolyl |
| R 51 | 4-Imidazolyl |
| R 52 | 5-Imidazolyl |
| R 53 | 3-Pyrazolyl |
| R 54 | 4-Pyrazolyl |
| R 55 | 2-Pyrazinyl |
| R 56 | 2-Pyrimidinyl |
| R 57 | 4-Pyrimidinyl |
| R 58 | 5-Pyrimidinyl |
| R 59 | 2-Pyridazinyl |
| R 60 | 3-Pyridazinyl |
| R 61 | 2-Dihydropyranyl |
| R 62 | 3-Dihydropyranyl |
| R 63 | 4-Dihydropyranyl |
| R 64 | 2-Dioxolanyl |
| R 65 | 3-Dioxolanyl |
| R 66 | 4-[1,2,3-Thiadiazolyl] |
| R 67 | 5-[1,2,3-Thiadiazolyl] |
| R 68 | 4-[1,2,3-Oxadiazolyl] |
| R 69 | 5-[1,2,3-Oxadiazolyl] |
| R 70 | 3-[1,2,4-Oxadiazolyl] |
| R 71 | 5-[1,3,4-Oxadiazolyl] |
| R 72 | 2-[1,3,4-Oxadiazolyl] |
| R 73 | 5-[1,3,4-Oxadiazolyl] |
| R 74 | 2-[1,3-Dioxinyl] |
| R 75 | 4-[1,3-Dioxinyl] |
| R 76 | 5-[1,3-Dioxinyl] |
| R 77 | 6-[1,3-Dioxinyl] |
| R 78 | 2-[1,3-Dioxanyl] |
| R 79 | 4-[1,3-Dioxanyl] |
| R 80 | 5-[1,3-Dioxanyl] |
| R 81 | 6-[1,3-Dioxanyl] |
| R 82 | 2-[1,4-Dioxanyl] |
| R 83 | 3-[1,4-Dioxanyl] |
| R 84 | 5-[1,4-Dioxanyl] |
| R 85 | 6-[1,4-Dioxanyl] |
| R 86 | 2-[1,3,5-Triazinyl] |
| R 87 | 4-[1,3,5-Triazinyl] |
| R 88 | 6-[1,3,5-Triazinyl] |
| R 89 | 3-[1,2,4-Triazinyl] |
| R 90 | 5-[1,2,4-Triazinyl] |
| R 91 | 6-[1,2,4-Triazinyl] |
| R 92 | 3-[1,2,4-Oxazinyl] |
| R 93 | 4-[1,2,4-Oxazinyl] |
| R 94 | 5-[1,2,4-Oxazinyl] |
| R 95 | 6-[1,2,4-Oxazinyl] |
| R 96 | 2-[1,3,2-Oxazinyl] |
| R 97 | 4-[1,3,2-Oxazinyl] |
| R 98 | 5-[1,3,2-Oxazinyl] |
| R 99 | 6-[1,3,2-Oxazinyl] |
| R 100 | 2-[1,3,6-Oxazinyl] |
| R 101 | 4-[1,3,6-Oxazinyl] |
| R 102 | 5-[1,3,6-Oxazinyl] |
| R 103 | 6-[1,3,6-Oxazinyl] |
| R 104 | 3-[1,2,6-Oxazinyl] |
| R 105 | 4-[1,2,6-Oxazinyl] |
| R 106 | 5-[1,2,6-Oxazinyl] |
| R 107 | 6-[1,2,6-Oxazinyl] |
| R 108 | 2-[1,4-Oxazinyl] |
| R 109 | 3-[1,4-Oxazinyl] |
| R 110 | 5-[1,4-Oxazinyl] |
| R 111 | 6-[1,4-Oxazinyl] |
| R 112 | C$_6$H$_5$ |
| R 113 | 2-CH$_3$—C$_6$H$_4$ |
| R 114 | 2-C$_2$H$_5$—C$_6$H$_4$ |
| R 115 | 3-CH$_3$—C$_6$H$_4$ |
| R 116 | 4-CH$_3$—C$_6$H$_4$ |
| R 117 | 2-Cl—C$_6$H$_4$ |
| R 118 | 3-Cl—C$_6$H$_4$ |
| R 119 | 4-Cl—C$_6$H$_4$ |
| R 120 | 2-CF$_3$—C$_6$H$_4$ |
| R 121 | 3-CF$_3$—C$_6$H$_4$ |
| R 122 | 4-CF$_3$—C$_6$H$_4$ |
| R 123 | 2-CH$_3$O—C$_6$H$_4$ |
| R 124 | 3-CH$_3$O—C$_6$H$_4$ |
| R 125 | 4-CH$_3$O—C$_6$H$_4$ |
| R 126 | 3-CHF$_2$O—C$_6$H$_4$ |
| R 127 | 4-CHF$_2$O—C$_6$H$_4$ |
| R 128 | 3-CF$_3$O—C$_6$H$_4$ |
| R 129 | 4-CF$_3$O—C$_6$H$_4$ |
| R 130 | 3-CClF$_2$O—C$_6$H$_4$ |
| R 131 | 4-CClF$_2$O—C$_6$H$_4$ |
| R 132 | 3-CH$_3$S—C$_6$H$_4$ |
| R 133 | 4-CH$_3$S—C$_6$H$_4$ |
| R 134 | 3-CHF$_2$S—C$_6$H$_4$ |
| R 135 | 4-CHF$_2$S—C$_6$H$_4$ |
| R 136 | 3-CClF$_2$S—C$_6$H$_4$ |
| R 137 | 4-CClF$_2$S-C$_6$H$_4$ |
| R 138 | 2-NO$_2$—C$_6$H$_4$ |
| R 139 | 3-NO$_2$—C$_6$H$_4$ |
| R 140 | 4-NO$_2$—C$_6$H$_4$ |
| R 141 | 2-CN—C$_6$H$_4$ |
| R 142 | 3-CN—C$_6$H$_4$ |
| R 143 | 4-CN—C$_6$H$_4$ |
| R 144 | 2-F—C$_6$H$_4$ |
| R 145 | 3-F—C$_6$H$_4$ |
| R 146 | 4-F—C$_6$H$_4$ |
| R 147 | 3,4-Cl$_2$—C$_6$H$_4$ |
| R 148 | 3-Cl-4-CH$_3$O—C$_6$H$_4$ |
| R 149 | 3-Cl-4-CH$_3$—C$_6$H$_4$ |
| R 150 | 2,4,6-Cl$_3$—C$_6$H$_4$ | and the heterocycles and bialicycles N1 to 317 mentioned at A

| Comp. No. | |
|---|---|
| | $R^5$ |
| S 1 | H |
| S 2 | $CH_3$ |
| S 3 | $C_2H_5$ |
| S 4 | n-$C_3H_7$ |
| S 5 | i-$C_3H_7$ |
| S 6 | n-$C_4H_9$ |
| S 7 | i-$C_4H_9$ |
| S 8 | sec.-$C_4H_9$ |
| S 9 | tert.-$C_4H_9$ |
| S 10 | n-$C_5H_{11}$ |
| S 11 | $CH[CH_3]C_3H_7$ |
| S 12 | $CH_2CH[CH_3]C_2H_5$ |
| S 13 | $[CH_2]_2CH[CH_3]CH_3$ |
| S 14 | $C[CH_3]_2C_2H_5$ |
| S 15 | $CH[CH_3]CH[CH_3]CH_3$ |
| S 16 | $CH_2-C[CH_3]_2CH_3$ |
| S 17 | $CH[C_2H_5]C_2H_5$ |
| S 18 | n-$C_6H_{13}$ |
| S 19 | $CH[CH_3]C_4H_9$ |
| S 20 | $CH_2CH[CH_3]C_3H_7$ |
| S 21 | $[CH_2]_2CH[CH_3]C_2H_5$ |
| S 22 | $[CH_2]_3CH[CH_3]CH_3$ |
| S 23 | $C[CH_3]_2C_3H_7$ |
| S 24 | $CH[CH_3]CH]CH_3]C_2H_5$ |
| S 25 | $CH[CH_3]CH_2CH[CH_3]_2$ |
| S 26 | $CH_2-C[CH_3]_2C_2H_5$ |
| S 27 | $CH_2CH[CH_3]CH[CH_3]_2$ |
| S 28 | $[CH_2]_2C[CH_3]_2CH_3$ |
| S 29 | $CH[C_2H_5][CH_2]_2CH_3$ |
| S 30 | $CH_2CH[C_2H_5]C_2H_5$ |
| S 31 | $CH[CH_3]C[CH_3]_2CH_3$ |
| S 32 | $CH[CH_3]CH[CH_3]CH_2CH_3$ |
| S 33 | $C[CH_3, C_2H_5]C_2H_5$ |
| S 34 | $C[C_2H_5]CH[CH_3]_2$ |
| S 35 | $CH_3O$ |
| S 36 | $C_2H_5O$ |
| S 37 | n-$C_3H_7O$ |
| S 38 | i-$C_3H_7O$ |
| S 39 | n-$C_4H_9O$ |
| S 40 | i-$C_4H_9O$ |
| S 41 | sec.-$C_4H_9O$ |
| S 42 | tert.-$C_4H_9O$ |
| S 43 | $CH_2OCH_3$ |
| S 44 | $CH_2OC_2H_5$ |
| S 45 | $[CH_2]_2OCH_3$ |
| S 46 | $[CH_2]_2OC_2H_5$ |
| S 47 | $[CH_2]_3OCH_3$ |
| S 48 | $[CH_2]_3OC_2H_5$ |
| S 49 | $[CH_2]_3O$-n-$C_3H_7$ |
| S 50 | cycl.-$C_3H_5$ |
| S 51 | cycl.-$C_4H_7$ |
| S 52 | cycl.-$C_5H_9$ |
| S 53 | cycl.-$C_6H_{11}$ |
| | $R^6$ |
| T 1 | H |
| T 2 | $CH_3$ |
| T 3 | $C_2H_5$ |
| T 4 | n-$C_3H_7$ |
| T 5 | i-$C_3H_7$ |
| T 6 | n-$C_4H_9$ |
| T 7 | i-$C_4H_9$ |
| T 8 | sec.-$C_4H_9$ |
| T 9 | tert.-$C_4H_9$ |

MANUFACTURING EXAMPLES

1. S(+)2-Amino-4-chloro-6-[1-cyclohexylethylamino]pyrimidine 17.0 g of S(+)-1-cyclohexylethylamine and 13.5 g of triethylamine are added to a mixture of 20 g of 2-amino-4,6-dichloropyrimidine in 250 ml of 1-propanol, and the whole is refluxed for 7 hours. The reaction mixture is evaporated down under reduced pressure, and the residue is partitioned between ethyl acetate and water. The aqueous phase is again extracted with ethyl acetate, and the whole organic phase is then washed once with water, dried over magnesium sulfate, and evaporated down under reduced pressure, finally at 90° C./0.3 mbar. There is obtained 28.6 g of the title compound of m.p. 59°-63° C., $[\alpha]_D^{20} = +3.741°$ ($CH_2Cl_2$)—active ingredient example 1.01

2. 4-Chloro-6-(furan-2-yl)methylamino-2-methoxyaminopyrimidine a) Manufacture of 4,6-dichloro-2-methoxyaminopyrimidine:

40 g (0.48 mol) of O-methylhydroxylamine hydrochloride is added to a solution of 100 g (0.44 mol) of 4,6-dichloro-2-methylsulfonylpyrimidine in 400 ml of N,N-dimethylformamide. 66 g (0.48 mol) of potassium carbonate is added and the whole is heated at 90° C. for 10 hours. The mixture is allowed to cool, is evaporated down, the residue is taken up in 10% strength aqueous hydrochloric acid and dichloromethane, the phases are separated, dried and concentrated in a rotary evaporator. The 4-chloro-6-methoxyamino-2-methylsulfonylpyrimidine obtained as byproduct may be separated by chromatography on silica gel (developer: cyclohexane/ethyl acetate). There is obtained 39 g (45%) of the title compound as a white crystalline mass of m.p. 135° C.

b) Preparation of 4-chloro-6-(furan-2-yl)methylamino-2-methoxyaminopyrimidine:

1.14 g (8.5 mmol) of furfurylamine hydrochloride and then 1.6 g (16 mmol) of triethylamine are added to a solution of 1.5 g (7.7 mmol) of 4,6-dichloro-2-methoxyaminopyrimidine in 10 ml of n-propanol. The mixture is refluxed for 8 hours and evaporated down; the residue is taken up with water and dichloromethane and neutralized with 10% strength hydrochloric acid, the phases are separated and extracted twice with dichloromethane, and the combined extracts are dried and evaporated down. There remains as residue 1.8 g (92%) of the title compound as a brown oil.

$^1$H-NMR ($CDCl_3$, 250 MHz) $\delta = 3.85$ (s; 3H), 4.50 (s; 2H), 6.00 (s; 1H), 6.20–6.35 (m; 2H), 7.35 (d; 1H), 8.20 (s, broad; 1H) Active ingredient example 1.02

3. 2-Amino-4-chloro-6-[3-(1-methylethyl)-isoxazol-5-yl]-methylaminopyrimidine 8.0 g (44 mmol) of 2-amino-4-chloro-6-(propyn-3-yl)aminopyrimidine in 5 ml of tetrahydrofuran is cooled to 0° C.; 5.3 g (44 mmol) of isobutyrylhydroxamyl chloride and then 8.9 g (88 mmol) of triethylamine are added. The mixture is stirred for 14 hours at room temperature and taken up with dichloromethane and water, the phases are separated, and the organic phase is dried, evaporated down and purified by chromatography on silica gel (developer: cyclohexane/ethyl acetate). There is obtained 6.8 g (58%) of the title compound as a highly viscous oil.

$^1$H-NMR ($CDCl_3$; 250 MHz) $\delta = 1.25$ (d, 6H), 3.05 (sept; 1H), 4.65 (d; 2H), 5.15 (s, broad; 2H), 5.45 (s; broad; 1H), 5.85 (s; 1H), 6.05 (s; 1H)

active ingredient example 1.27

The pyrimidine derivatives of the formula I listed in the following Tables 1 to 3 were obtained by the processes described in Examples 1 to 3:

TABLE 1
Pyrimidine derivatives of the formula I
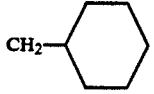
| Comp. No. | A | Y | mp [°C.], ¹H-NMR in CDCl₃ [ppm] |
|---|---|---|---|
| 1.04 | 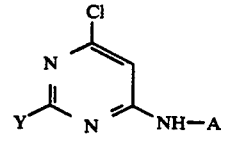 | NH₂ | 105–108 |
| 1.05 |  | NH₂ | 98–100 |
| 1.06 |  | C₂H₅NH | 50–52 |
| 1.07 | 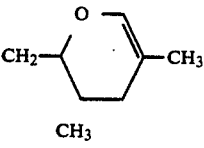 | NH₂ | 166–168 |
| 1.08 | 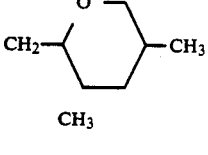 | NH₂ | 156–158 |
| 1.09 | 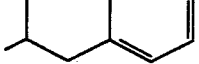 | NH₂ | 170–173 |
| 1.10 |  | NH₂ | 166–169 |
| 1.11 | 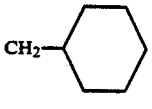 | C₂H₅NH | 87–90 |
| 1.12 | 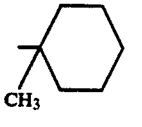 | NH₂ | 145 |
| 1.13 | 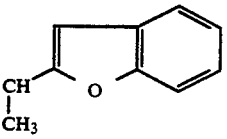 | NH₂ | 184–187 |
TABLE 1-continued
Pyrimidine derivatives of the formula I
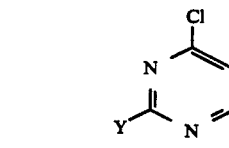
| Comp. No. | A | Y | mp [°C.], ¹H-NMR in CDCl₃ [ppm] |
|---|---|---|---|
| 1.14 | 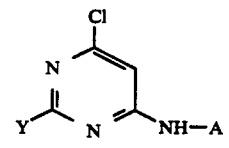 | NH₂ | 80–86 |
| 1.15 | 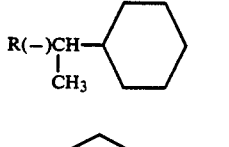 | NH₂ | 168 $[\alpha]_D^{20}$ −4.740° [CH₂Cl₂] |
| 1.16 | 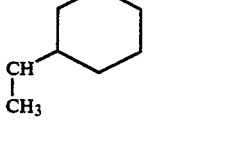 | NH₂ | 96–104 |
| 1.17 | 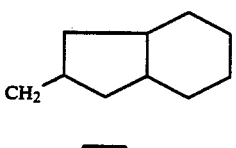 | NH₂ | 113–116 |
| 1.18 | 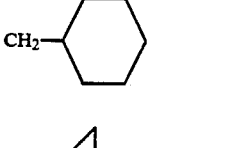 | NH₂ | 102–108 |
| 1.19 | 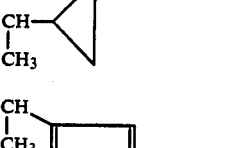 | NH₂ | resin ¹H-NMR [d₆DMSO] CH₃ at 1.1 ppm d; 3H |
| 1.20 | 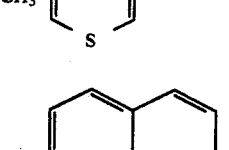 | NH₂ | 143–146 |
| 1.21 | 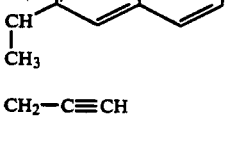 | NH₂ | 134–137 |
| 1.22 | CH₂—C≡CH | NHOCH₃ | 100–102 |
| 1.23 | 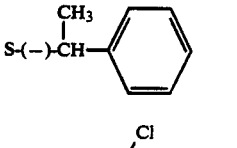 | NHOCH₃ | 93–95 |
| 1.24 | 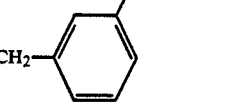 | NHOCH₃ | 92 |

TABLE 1-continued

Pyrimidine derivatives of the formula I

Structure: 6-chloro-pyrimidine with Y at 2-position and NH—A at 4-position

| Comp. No. | A | Y | mp [°C], $^1$H-NMR in CDCl$_3$ [ppm] |
|---|---|---|---|
| 1.25 | —CH$_2$-(furan-2-yl) | NHOCH$_3$ | 3.85 ppm (s, 3H) OCH$_3$ |
| 1.26 | —CH(CH$_3$)-cyclopropyl | NHOCH$_3$ | 1.15 (d, 3H) CH$_3$ |
| 1.27 | —CH$_2$-(3-ethylisoxazol-5-yl) | NH$_2$ | 3.05 (s, 1H) CH(CH$_3$)$_2$ |
| 1.28 | —CH(CH$_3$)-(tetrahydrofuran-2-yl) | NH$_2$ | 110–117 |
| 1.29 | —CH(CH$_2$CH$_3$)-(chroman-3-yl) | NH$_2$ | 105 |
| 1.30 | —CH$_2$-(tetrahydrofuran-2-yl) | NH$_2$ | 129–132 |
| 1.31 | —CH(CH$_3$)-(thiophen-3-yl) | NHOCH$_3$ | 1.6(d, 3H); 3.8(s, 3H); 4.8–5.1 (m, 1H); 5.25–5.55 (m, 1H); 5.9(s, 1H); 7.05(d, 1H); 7.15(d, 1H); 7.35(dd, 1H); 7.5 (s, br, 1H) |
| 1.32 | —CH$_2$-(tetrahydrofuran-2-yl) | NHOCH$_3$ | 1.8–2.15 (m, 4H); 3.0–4.2 (m, 6H); 3.90(s, 3H); 6.15(s, 1H); 9.15(s, br, 1H) |
| 1.33 | —CH$_2$-(decahydronaphthalen-1-yl) | NHOCH$_3$ | 1.10–2.10 (15H); 2.9–3.35 (m, 3H); 3.80(s, 3H); 5.90(s, 1H); 7.9(s, br, 1H) |
| 1.34 | —CH$_2$-(naphthalen-1-yl) | NHOCH$_3$ | 114–116 |
| 1.35 | —CH(CH$_3$)-(pyridin-4-yl) | NH$_2$ | 1.37–1.42 (d/3H) 6.4(s/2H; NH$_2$) 7.65–7.7 (d/1H; NH) |

TABLE 2

Pyrimidine derivatives of the formula I where X = OCF$_3$

Structure: 6-(OCF$_3$)-pyrimidine with Y at 2-position and NH—A at 4-position

| Comp. No. | A | Y | mp [°C], $^1$H-NMR in CDCl$_3$ [ppm] |
|---|---|---|---|
| 2.01 | S(—)—CH(CH$_3$)-phenyl | NH$_2$ | resin; 5.35 ppm (s/1H) NH; 5.25 ppm (s/1H) Pyr—CH; 4.95 ppm (s/2H) NH$_2$; 1.55 ppm (d/3H) CH$_3$ |
| 2.02 | H$_3$C—CH-(thiophen-3-yl) | NH$_2$ | resin; 5.31 (s/1H) Pyr—CH; 5.15 (s/1H) NH; 4.88 (s/2H) NH$_2$; 1.50 (d/3H) CH$_3$ |
| 2.03 | —CH(CH$_3$)-(benzofuran-2-yl) | NH$_2$ | resin; 6.52 (2/1H) Fur—CH; 5.4 (s/1H) Pyr—CH; 5.34 (s/1H) NH; 5.05 (s/2H) NH$_2$; 1.60 (d/3H) CH$_3$ |
| 2.04 | —CH(CH$_3$)-cyclopropyl | NH$_2$ | 80–82 |

TABLE 3

Pyrimidine derivatives of the formula I where X = CF₃

![structure with CF3, N, Y, N, NH-A on pyrimidine]

| Comp. No. | A | Y | mp [°C], ¹H-NMR in CDCl₃ [ppm] |
|---|---|---|---|
| 3.01 | S(−)−CH(CH₃)−phenyl | NH₂ | 1.65(d, 3H); 4.95(s, 1H); 5.05–5.35(m,/1H9; 6.0 (s, 1H); 7.2–7.4(m, 5H) |
| 3.02 | −CH(CH₃)−(thiophen-2-yl) | NH₂ | 1.55(d, 3H); 3.55–3.7 (m, 1H); 5.35(s, br, 3H); 7.05(d, 1H); 7.15(d, 1H), 7.3(dd, 1H) |
| 3.03 | −CH₂−(naphthyl) | NH₂ | 191–193 |
| 3.04 | −CH₂−(tetrahydrofuran-2-yl) | NH₂ | 177–179 |
| 3.05 | −CH(CH₃)−cyclopropyl | NH₂ | 0.15–0.4(m, 2H); 0.45–0.6(m, 2H); 0.8–1.0(m, 1H); 3.25–3.55(m, 1H); 5.0–5.6(s, br, 3H); 6.05(s, 1H); |
| 3.06 | −CH(CH₃)−cyclohexyl | NH₂ | 159–162 |
| 3.07 | indanyl | NH₂ | 226–228 |
| 3.08 | 3-methoxyphenyl | NH₂ | 252–253 |

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water.

The pots were set up in the greenhouse in accordance with the requirements specific to their species, i.e., 20° to 35° C., or 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Alopercurus myosuroides, Avena fatua, Abutilon theophrasti, Amaranthus retroflexus, Cassia tora* and *Sinapis alba*.

Compound 1.19, applied postemergence at a rate of 0.75 kg/ha, provides excellent control of broadleaved unwanted plants and harmful grasses.

It is clear from the following comparative experiments that the pyrimidine derivatives according to the invention not only have a stronger herbicidal action on harmful plants but are also better tolerated by crop plants than prior art pyrimidine derivatives, e.g., comparative substances A and B

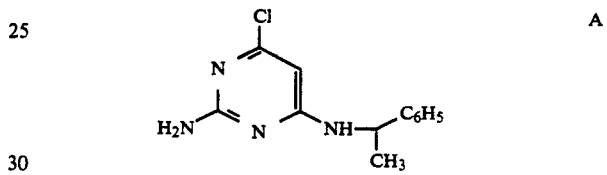

A disclosed in DE-A 37 17 480, Example 63

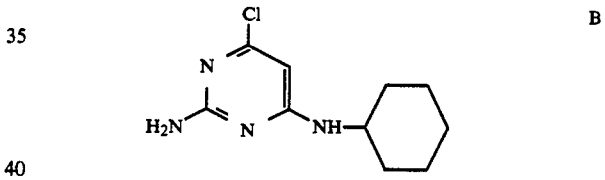

B disclosed in DE-A 20 65 629, Example 5.

TABLE I

Examples illustrating the control of unwanted broadleaved plants and tolerance by a crop plant on postemergence application of 0.375 and 0.19 kg/ha in the greenhouse

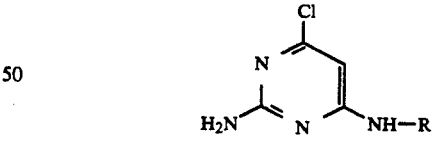

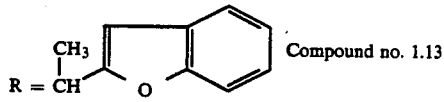

Compound no. 1.13, R = CH(CH₃)−(benzofuran-2-yl)

R = C(H)(CH₃)−Phenyl   Comparative substance A

| | Damage in % | | | |
|---|---|---|---|---|
| | Compound 1.13 | | Compound A | |
| Test plants | 0.375 kg/ha | 0.19 kg/ha | 0.375 kg/ha | 0.19 kg/ha |
| *Hordeum vulgaris* | 20 | 0 | 80 | 60 |
| *Amaranthus refroflexus* | 100 | 100 | 100 | 100 |
| *Polygonum persicaria* | 100 | 100 | 100 | 100 |

TABLE I-continued

| Viola arvensis | 70 | 70 | 40 | 20 |
|---|---|---|---|---|

TABLE II

Examples illustrating control of unwanted broadleaved plants and tolerance by a crop on postemergence application of 0.375 and 0.19 kg/ha in the greenhouse

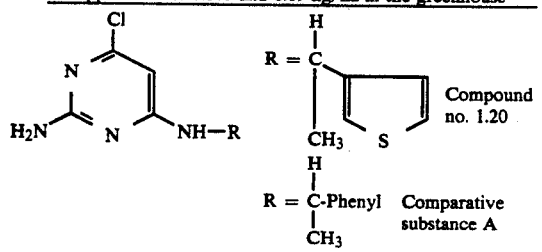

Compound no. 1.20

R = C-Phenyl  Comparative substance A
       |
      CH₃

| Test plants | Damage in % | | | |
|---|---|---|---|---|
| | Compound 1.20 | | Compound A | |
| | 0.375 kg/ha | 0.19 kg/ha | 0.375 kg/ha | 0.19 kg/ha |
| Arachis hypogaea | 20 | 10 | 40 | 40 |
| Amaranthus refroflexus | 100 | 100 | 100 | 100 |
| Cassia tora | 100 | 100 | 100 | 90 |
| Chrysanthemum | 100 | 100 | 100 | 70 |

TABLE III

Examples illustrating control of unwanted broadleaved plants on postemergence application of 0.5 and 0.25 kg/ha in the greenhouse

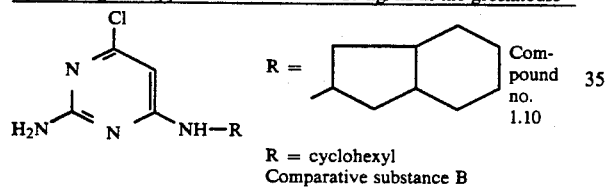

Compound no. 1.10

R = cyclohexyl
Comparative substance B

| Test plants | Damage in % | | | |
|---|---|---|---|---|
| | Compound 1.10 | | Compound B | |
| | 0.5 kg/ha | 0.25 kg/ha | 0.5 kg/ha | 0.25 kg/ha |
| Abuthilon theophrasti | 100 | 100 | 0 | 0 |
| Chenopodium album | 100 | 100 | 100 | 70 |
| Ipomoea spp. | 100 | 100 | 50 | 20 |

We claim:

1. A pyrimidine derivative of the formula Ia

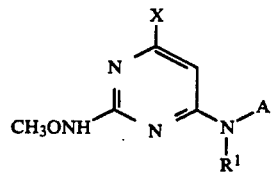

where
$R^1$ is hydrogen or $C_1-C_4$-alkyl;
A is selected from the group consisting of 2-, 3-, 4-, 5-, 6- and 7-benzofuryl, 1-, 3-, 4-, 5-, 6- and 7-isobenzofuryl, 2-, 3-, 4-, 5-, 6- and 7-benzo[b]thienyl, 1-, 3-, 4-, 5-, 6- and 7-benzo[c]thienyl, 2-, 3-, 4-, 5-, 6- and 7-indolyl, 1-, 3-, 4-, 5-, 6- and 7-isoindolyl, 3-, 4-, 5-, 6- and 7-benzo[c]isoxazolyl, 3-, 4-, 5-, 6- or 7-benzo[b]isoxazolyl, 3-, 4-, 5-, 6- or 7-benzo[c]isothiazolyl, 3-, 4-, 5-, 6- or 7-benzo[b]isothiazolyl, 3-, 4-, 5-, 6- or 7-benzo[b]pyrazolyl, 3-, 4-, 5-, 6- or 7-benzo[c]pyrazolyl, 2-, 4-, 5-, 6- or 7-benzoxazolyl, 2-, 4-, 5-, 6-or 7-benzothiazolyl, 2-, 4-, 5- or 6-benzimidazolyl, 2,3-dihydrobenzofur-2-, 3-, 4-, 5-, 6- or 7-yl, 1,3-dihydroisobenzofur-1-, 3-, 4-, 5-, 6- or 7-yl, 2,3-dihydrobenzo[b]thien-2-, 3-, 4-, 5-, 6- or 7-yl, 1,3-dihydrobenzo[c]thien-1-, 3-, 4-, 5-, 6- or 7-yl, [1,3-dihydrobenzo[c]thien-1-,3-, -4-, 5-, 6-, or 7-yl,] 1,3-dihydroisoindol-1-, 3-, 4-, 5-, 6- or 7-yl, 2,3-dihydroindol-2-, 3-, 4-, 5-, 6- or 7-yl, 2-, 3-, 4-, 5-, 6-, 7- or 8-chromenyl, 1-, 3-, 4-, 5-, 6-, 7- or 8-isochromenyl, 2-, 3-, 4-, 5-, 6-, 7- or 8-quinolyl, 1-, 3-, 4-, 5-, 6-, 7- or 8-isoquinolyl, 2-, 3-, 4-, 5-, 6-, 7- or 8-chromanyl, 1-, 3-, 4-, 5-, 6-, 7- or 8-isochromanyl, 3-, 4-, 5-, 6-, 7- or 8-cinnolinyl, 1-, 4-, 5-, 6-, 7- or 8-phthalazinyl, 2-, 3-, 5-, 6-, 7- or 8-quinoxalinyl, 2-, 4-, 5-, 6-, 7- or 8-quinazolinyl, 3-, 5-, 6-, 7- or 8-benzo-1,2,4-triazinyl, 2-, 3-, 4-, 5-, 6- or 7-benzopyranyl, 2-, 3-, 4-, 5-, 6- or 7-naphthpyridinyl, 2-, 3-, 4-, 6-, 7- or 8-pyrido[3,2-b]pyridinyl, 2-, 3-, 4-, 5-, 7- or 8-pyrido[4,3-b]pyridinyl, 2-, 3-, 4-, 5-, 6-or 8-pyrido[3,4-b]pyridinyl, 1,3,2-benzoxazin-2-, 4-, 5-, 6-, 7- or 8-yl, 1,4,2-benzoxazin-2-, 3-, 5-, 6-, 7- or 8-yl, 2,3-1-benzoxazin-1-, 4-, 5-, 6-, 7- or 8-yl, 3,1,4-benzoxazin-2-, 4-, 5-, 6-, 7- or 8-yl, 1,2-benzisoxazin-3-, 4-, 5-, 6-, 7- or 8-yl, 1,4-benzisoxazin-2-, 5-, 6-, 7- or 8-yl, 2-, 6- or 8-purinyl, 1-, 2-, 3-, 4-, 5-, 6- or 7-indanyl, 1-, 2-, 3-, 4-, 5-, 6- or 7-indenyl, 1-, 2-, 3-, 4-, 5-, 6-, 7- or 8-tetralinyl, 1-, 2-, 3-, 4-, 5-, 6-, 7- or 8-decalinyl, 3-, 4-, 5-, 6-, 7-, 8-, 9- or 10-tricyclo[5.2.1.0²,⁶]decanyl, 3-, 4-, 5-, 7-, 8-, 9- or 10-tricyclo[5.2.1.0²,⁶]dec-²,⁶-enyl, 1- or 2-norbornyl, 2-bornyl, 2- or 3-norpinyl, 1-, 2-, 3-, 4-, 5-, 6-, 7-, 8- or 9-fluorenyl or 1-, 2-, 3-, 4-, 5-, 6-, 7- or 8-naphthyl, where the stated radicals may carry the following groups: $C_1-C_3$-alkyl, $C_1-C_3$-alkoxy or halogen; A may further more be $CR^2R^3R^4$, where $R^2$ is hydrogen and $R^3$ is hydrogen or $C_1-C_4$-haloalkyl, and $R^4$ is an unsubstituted or methyl, methoxy or chlorine substituted radical, selected from the group consisting of: naphthyl and $C_3-C_8$-cycloalkyl, or is unsubstituted or substituted mono-or bicyclic heterocyclyl selected from the group consisting of 2-furyl, 2-thienyl, 2-pyrrolyl, 2-N-methylpyrrolyl, 2- and 3-pyridyl, 2-thiolanyl, 2-perhydropyrrolyl, 2-perhydro-N-methylpyrrolyl, 2,3-tetrahydrofuryl, 3-furyl, 3-perhydropyrrolyl, 3pyrrolyl, 3-thiolanyl, 3-thienyl, 2-, 3- or 4-pyranyl, 2-, 3- or 4-dihydropyranyl, 2-, 3- or 4-tetrahydropyranyl, 2-, 3- or 4-thiopyranyl, 2-, 3- or 4-tetrahydrothiopyranyl, 4-pyridyl, 3-, 4- or 5-isoxazolyl, 3-, 4- or 5-isothiazolyl, 2-, 4- or 5-oxazolyl, 2-, 4- or 5-thiazolyl, 2-, 4- or 5-imidazolyl, 3- or 4-pyrazolyl, 2-pyrazinyl, 2-, 4- or 5- pyrimidinyl, 2- or 3-pyridazinyl, 2- or 3-dioxolanyl, 1,2,3-thiadiazol-4- or 5-yl,1,2,4-oxadiazol-3- or 5-yl, 1,3,4-oxadiazol-2- or 5-yl, 1,2,3-oxadiazol-4- or 5-yl, 1,3-dioxin-2-, 4-, 5- or 6-yl, 1,3-dioxan-2-, 4-, 5- or 6-yl, 1,4-dioxan-2-, 3-, 5- or 6-yl, 1,3,5-triazin-2-, 4- or 6-yl, 1,2,4-triazin-3-, 5- or 6-yl, 1,2,4-oxazin-3-, 4-, 5- or 6-yl, 1,3,2-oxazin-2-, 4-, 5- or 6-yl, 1,3,6-oxazin-2-, 4-, 5- or 6-yl, 1,2,6-oxazin-3-, 4-, 5- or 6-yl or 1,4-oxazin-2-, 3-, 5- or 6-yl, or the heterocycles and alibicycles stated for A, where the stated radicals may carry the following groups: methyl, ethyl, trifluoromethyl, methoxy, ethoxy, difluoromethoxy, trifluoromethoxy, chlorodifluromethoxy, methylthio, difluoromethylthio, trifluoromethylthio, chlorodifluoromethylthio or halogen;

$R^4$ is furthermore $C_2-C_6$-alkyl, $C_2-C_6$-alkenyl or $C_2-C_6$-alkinyl if X is chlorine or $C_1-C_3$-haloalkyl; and X is halogen, $C_1-C_3$-haloalkyl, $C_1-C_3$-haloalkoxy, and addition salts thereof with organic or inorganic acids.

2. A pyrimidine derivative of the formula Ia as defined in claim 1 where $R^1$ is hydrogen;

X is chlorine;

A is a $CHR^3R^4$ group;

$R^3$ is hydrogen or $C^1-C^4$-alkyl;

$R^4$ is 1-naphthyl, $C_3-C_8$-cycloalkyl, 2-furyl, 3-(1-methylethyl)isooxazol-5-yl, 3-thienyl, 3-tetrahydrofuryl or 2-tetrahydroindanyl.

3. A herbicidal composition, in addition to inert additives, one or more pyrimidine derivatives of the formula Ia where the substituents have the meanings stated in claim 1.

4. A method for controlling undesirable plant growth, wherein the undesirable plants or the area to be treated kept free from undesirable plant growth is or are treated with a herbicidally effective amount of a pyrimidine derivative of the formula as claimed in claim 1.

5. A pyrimidine derivative of the formula Ib

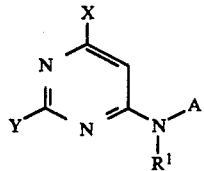

where $R^1$ is hydrogen or $C_1-C_5$-alkyl;

A is selected from the group consisting of 2-, 3-, 4-, 5-, 6- and 7-benzofuryl, 1-, 3-, 4-, 5-, 6- and 7-isobenzofuryl, 2-, 3-, 4-, 5-, 6- and 7-benzo[b]thienyl, 1-, 3-, 4-, 5-, 6- and 7-benzo[c]thienyl, 2-, 3-, 4-, 5-, 6-and 7-indolyl, 1-, 3-, 4-, 5-, 6- and 7-isoindolyl, 3-, 4-, 5-, 6- and 7-benzo[c]isoxazolyl, 3-, 4-, 5-, 6- or 7-benzo[b]isoxazolyl, 3-, 4-, 5-, 6- or 7-benzo[c]isothiazolyl, 3-, 4-, 5-, 6- or 7-benzo[b]isothiazolyl, 3-, 4-, 5-, 6- or 7-benzo[b]pyrazolyl, 3-, 4-, 5-, 6- or 7-benzo[c]pyrazolyl, 2-, 4-, 5-, 6- or 7-benzoxazolyl, 2-, 4-, 5-, 6- or 7-benzothiazolyl, 2-, 4-, 5- or 6-benzimidazolyl, 2,3-dihydrobenzofur-2-, 3-, 4-, 5- 6- or 7-yl, 1,3-dihydroisobenzofur-1-, 3-, 4-, 5-, 6-or 7-yl, 2,3-dihydrobenzo[b]thien-2-, 3-, 4-, 5-, 6- or 7-yl, 1,3-dihydrobenzo[c]thien-1-, 3-, 4-, 5-, 6- or 7-yl, 1,3-dihydrobenzo[c]thien-1-, 3-, 4-, 5-, 6- or 7-yl, 1,3-dihydroisoindol-1-, 3-, 4-, 5-, 6- or 7-yl, 2,3-dihydroindol-2-, 3-, 4-, 5-, 6- or 7-yl, 2-, 3-, 4-, 5-, 6-, 7-or 8-chromenyl, 1-, 3-, 4-, 5-, 6-, 7- or 8-isochromenyl, 2-, 3-, 4-, 5-, 6-, 7- or 8-quinolyl, 1-, 3-, 4-, 5-, 6-, 7- or 8-isoquinolyl, 2-, 3-, 4-, 5-, 6-, 7- or 8-chromanyl, 1-, 3-, 4-, 5-, 6-, 7- or 8-isochromanyl, 3-, 4-, 5-, 6-, 7- or 8-cinnolinyl, 1-, 4-, 5-, 6-, 7- or 8-phthalazinyl, 2-, 3-, 5-, 6-, 7- or 8-quinoxalinyl, 2-, 4-, 5-, 6-, 7- or 8-quinazolinyl, 3-, 5-, 6-, 7- or 8-benzo-1,2,4-triazinyl, 2-, 3-, 4-, 5-, 6- or 7-benzopyranyl, 2-, 3-, 4-, 5-, 6- or 7-naphthpyridinyl, 2-, 3-, 4-, 6-, 7- or 8-pyrido[3,2-b]pyridinyl, 2-, 3-, 4-, 5-, 7- or 8-pyrido[4,3-b]pyridinyl, 2-, 3-, 4-, 5-, 6- or 8-pyrido[3,4-b]pyridinyl, 1,3,2-benzoxazin-2-, 4-, 5-, 6-, 7- or 8-yl, 1,4,2-benzoxazin-2-, 3-, 5-, 6-, 7- or 8-yl, 2,3-1-benzoxazin-1-, 4-, 5-, 6-, 7- or 8-yl, 3,1,4-benzoxazin-2-, 4-, 5-, 6-, 7- or 8-yl, 1,2-benzisoxazin-3-, 4-, 5-, 6-, 7- or 8-yl, 1,4-benzisoxazin-2-, 3-, 5-, 6-, 7- or 8-yl, 2-, 6- or 8-purinyl, 1-, 2-, 3-, 4-, 5-, 6- or 7-indanyl, 1-, 2-, 3-, 4-, 5-, 6- or 7-indenyl, 1-, 2-, 3-, 4-, 5-, 6-, 7- or 8-tetralinyl, 1-, 2-, 3-, 4-, 5-, 6-, 7- or 8-decalinyl, 3-, 4-, 5-, 6-, 7-, 8-, 9-, or 10-tricyclo[5.2.1.0$^{2,6}$]decanyl, 3-, 4-, 5-, 7-, 8-, 9-or 10-tricyclo[5.2.1.0$^{2,6}$]dec-$^{2,6}$-enyl, 1- or 2-norbornyl, 2-bornyl, 2- or 3-norpinyl, 1-, 2-, 3-, 4-, 5-, 6-, 7-, 8- or 9-fluorenyl or 1-, 2-, 3-, 4-, 5-, 6-, 7- or 8-naphthyl, where the stated radicals may carry the following groups: $C_1-C_3$-alkyl, $C_1-C_3$-alkoxy or halogen;

A may furthermore be $CR^2R^3R^4$, where $R^2$ and $R^3$ are each hydrogen or $C_1-C_4$-alkyl, and $R^4$ is unsubstituted or methyl, methoxy or chlorine substituted naphthyl or $C_4-C_8$-cycloalkyl or cyclopropyl is Y is $NH_2$ and X is halogen or $C_1-C_3$-haloalkoxy;

mono- or bicyclic heterocyclyl having from one to three hetero atoms selected from the group consisting of 2,3-tetrahydrofuryl, 3-furyl, 3-perhydropyrrolyl, 3-pyrrolyl, 3-thiolanyl, 3-thienyl, 2-, 3- or 4-pyranyl, 2-, 3- or 4-dihydropyranyl, 2-, 3- or 4-tetrahydropyranyl, 2-, 3- or 4-thiopyranyl, 2-, 3- or 4-tetrahydrothiopyranyl, 4-pyridyl, 3-, 4- or 5-isoxazolyl, 3-, 4- or 5-isothiazolyl, 2-, 4- or 5-oxazolyl, 2-, 4- or 5-thiazolyl, 2-, 4- or 5-imidazolyl, 3- or 4-pyrazolyl, 2-pyrazinyl, 2-, 4- or 6-pyrimidinyl, 2- or 3-pyridazinyl, 2- or 3-dioxolanyl, 1,2,3-thiadiazol-4- or 6-yl, 1,2,3-oxadiazol-4-or 6-yl, 1,2,4-oxadiazol-3- or 5-yl, 1,3,4-oxadiazol-2- or 6-yl, 1,3-dioxin-2-, 4-, 5- or 6-yl, 1,3-dioxan-2-, 4-, 5- or 6-yl, 1,4-dioxan-2-, 3-, 5-or 6-yl, 1,3,5-triazin-2-, 4- or 6-yl, 1,2,4-triazin-3-, 5- or 6-yl, 1,2,4-oxazin-3-, 4-, 5- or 6-yl, 1,3,2-oxazin-2-, 4-, 5- or 6-yl, 1,3,6-oxazin-2-, 4-, 5- or 6-yl, 1,2,6-oxazin-3-, 4-, 5- or 6-yl or 1,4-oxazin-2-, 3-, 5-or 6-yl, 3-benzopyranyl, 1-indanyl and 2-indanyl, where the stated radicals may carry the following groups: methyl methoxy or chlorine, or phenyl if Y is $NH_2$ and at the same time X is $C_1-C_3$-haloalkyl or $C_1-C_3$-haloalkoxy, where the phenyl radical may carry the following groups: methyl, methoxy or chlorine X is halogen, $C_1-C_3$-haloalkyl, $C_1-C_3$-haloalkoxy, and Y is $NHR^5$ where $R^5$ is hydrogen or $C_1-C_6$-alkyl, and addition salts thereof with organic or inorganic acids.

6. A pyrimidine derivative of the formula Ib as defined in claim 5 where $R^1$ is hydrogen;

X is chlorine;

Y is $NH_2$;

A is a $CHR^3R^4$ group;

$R^3$ is hydrogen or $C_1-C_4$-alkyl;

$R^4$ is a 2-naphthyl, $C_3-C_8$-cycloalkyl, [bicyclo[2.2.1]hept-2-yl, 2-benzofuryl,] 3-thienyl, 2-tetrahydrofuryl, 2-idanyl, or 3-benzopyranyl.

7. A pyrimidine derivative of the formula Ib as defined in claim 5 where $R^1$ is hydrogen;

X is trifluoromethoxy;

Y is $NH_2$;

A is a $CHR^3R^4$ group;

$R^3$ is hydrogen or $C_1$-$C_4$-alkyl;

$R^4$ is a 1-naphthyl, $C_3$-$C_8$-cycloalkyl, phenyl, 3-thienyl, or 2-benzofuranyl.

8. A pyrimidine derivative of the formula Ib as defined in claim 5 where $R^1$ is hydrogen;

X is trifluoromethoxy;

Y is $NH_2$;

A is a $CHR^3R^4$ group;

$R^3$ is hydrogen or $C_1$-$C_4$-alkyl;

$R^4$ is a 1-naphthyl, $C_3$-$C_8$-cycloalkyl, phenyl, 3-thienyl, 2-tetrahydrofuryl or 1-indanyl.

9. A herbicidal composition, in addition to inert additives, one or more pyrimidine derivatives of the formula Ib, where the substituents have the meanings stated in claim 1.

10. A method for controlling undesirable plant growth, wherein the undesirable plants or the area to be treated kept free from undesirable plant growth is or are treated with a herbicidally effective amount of a pyrimidine derivative of the formula as defined in claim 5.

* * * * *

UNITED STATES PATENT AND TRADEMARK OFFICE
CERTIFICATE OF CORRECTION

PATENT NO. : 5,280,009
DATED : January 18, 1994
INVENTOR(S) : HAMPRECHT et al.

It is certified that error appears in the above-indentified patent and that said Letters Patent is hereby corrected as shown below:

Claim 1, column 30, lines 9-10, delete the following: "[1,3-dihydrobenzo[c]thien-1-, 3-, 4-, 5-, 6- or 7yl,]".

Claim 5, column 32, line 20, "is", first occurrence, should be --if--.

Claim 5, column 32, line 32, "2-, 4- or 6-" should be -- 2-, 4- or 5- --.

Claim 5, column 32, line 33, "or 6-yl", both occurrences, should be -- or 5-yl --.

Claim 5, column 32, line 35, at the beginning of the line, "6-yl" should be -- 5-yl --.

UNITED STATES PATENT AND TRADEMARK OFFICE
CERTIFICATE OF CORRECTION

PATENT NO. : 5,280,009
DATED : January 18, 1994
INVENTOR(S) : HAMPRECHT et al

It is certified that error appears in the above-indentified patent and that said Letters Patent is hereby corrected as shown below:

Claim 6, column 32, line 61, delete the following:
"[bicyclo[2.2.1-]hept-2-yl, 2-benzofuryl,]".

Signed and Sealed this

Twentieth Day of September, 1994

Attest:

BRUCE LEHMAN

*Attesting Officer*  *Commissioner of Patents and Trademarks*